United States Patent
Fukui et al.

(10) Patent No.: US 12,419,818 B2
(45) Date of Patent: *Sep. 23, 2025

(54) EXTERNAL PREPARATION

(71) Applicant: KAO CORPORATION, Tokyo (JP)

(72) Inventors: Takashi Fukui, Kawasaki (JP); Tomonari Okada, Tsukuba (JP); Noriko Tejima, Sumida-ku (JP); Keigo Kajiwara, Setagaya-ku (JP)

(73) Assignee: KAO CORPORATION, Tokyo (JP)

( * ) Notice: Subject to any disclaimer, the term of this patent is extended or adjusted under 35 U.S.C. 154(b) by 1074 days.

This patent is subject to a terminal disclaimer.

(21) Appl. No.: 17/417,645

(22) PCT Filed: Dec. 27, 2019

(86) PCT No.: PCT/JP2019/051469
§ 371 (c)(1),
(2) Date: Mar. 10, 2022

(87) PCT Pub. No.: WO2020/138431
PCT Pub. Date: Jul. 2, 2020

(65) Prior Publication Data
US 2022/0226212 A1    Jul. 21, 2022

(30) Foreign Application Priority Data

Dec. 27, 2018 (JP) ................................. 2018-244998
Dec. 27, 2018 (WO) .................. PCT/JP2018/048006

(51) Int. Cl.
| | | |
|---|---|---|
| A61Q 17/04 | (2006.01) | |
| A61K 8/04 | (2006.01) | |
| A61K 8/27 | (2006.01) | |
| A61K 8/29 | (2006.01) | |
| A61K 8/34 | (2006.01) | |
| A61K 8/36 | (2006.01) | |
| A61K 8/891 | (2006.01) | |
| A61K 8/92 | (2006.01) | |

(52) U.S. Cl.
CPC ................. *A61K 8/27* (2013.01); *A61K 8/04* (2013.01); *A61K 8/29* (2013.01); *A61K 8/342* (2013.01); *A61K 8/361* (2013.01); *A61K 8/891* (2013.01); *A61K 8/92* (2013.01); *A61Q 17/04* (2013.01)

(58) Field of Classification Search
None
See application file for complete search history.

(56) References Cited

U.S. PATENT DOCUMENTS

| | | |
|---|---|---|
| 6,200,680 B1 | 3/2001 | Takeda et al. |
| 2009/0186225 A1 | 7/2009 | Lee et al. |
| 2009/0320719 A1 | 12/2009 | Lee et al. |
| 2010/0015445 A1 | 1/2010 | Lee et al. |
| 2010/0271268 A1 | 10/2010 | Hosoda et al. |
| 2012/0027830 A1 | 2/2012 | Nakamura et al. |
| 2012/0231058 A1 | 9/2012 | Yi et al. |
| 2013/0189207 A1 | 7/2013 | Blomberg |
| 2013/0216834 A1 | 8/2013 | Hashimoto et al. |
| 2014/0017188 A1* | 1/2014 | Sarkar ..................... A61Q 5/12 514/772 |
| 2018/0263864 A1 | 9/2018 | Landa et al. |
| 2020/0368124 A1 | 11/2020 | Yoshida et al. |

FOREIGN PATENT DOCUMENTS

| | | | |
|---|---|---|---|
| AU | 2004203522 A1 | * | 2/2005 |
| CN | 101146745 A | | 3/2008 |
| CN | 101535419 A | | 9/2009 |
| CN | 101541681 A | | 9/2009 |
| CN | 113195060 A | | 7/2021 |
| EP | 2 233 127 B1 | | 5/2020 |
| JP | 62-4212 A | | 1/1987 |
| JP | 7-35325 B2 | | 4/1995 |
| JP | 7-173044 A | | 7/1995 |
| JP | 7-328421 A | | 12/1995 |
| JP | 10-95617 A | | 4/1998 |
| JP | 2003081762 A | * | 3/2003 |
| JP | 3442698 B2 | * | 9/2003 |
| JP | 2004-203768 A | | 7/2004 |
| JP | 2004-331509 A | | 11/2004 |
| JP | 2009-155623 A | | 7/2009 |

(Continued)

OTHER PUBLICATIONS

International Search Report issued Mar. 24, 2020 in PCT/JP2019/051469 filed Dec. 27, 2019, 3 pages.
Extended European Search Report issued Sep. 26, 2022 in European Patent Application No. 19905633.4, 8 pages.
"The Gentle Communication Between People and Chemistry", Sakai Chemical Industry Co., Ltd., Catalog for cosmetic ingredients, (with English Translation), 2015, 19 pages.
Soichiro Nobuoka, "Particle morphology and optical properties of pigments", Pigment Physics Lecture (Lecture 2), (Coloring material, 55, (10), 1982, pp. 758-765 (with English Translation).
Ishihara Sangyo Co., Ltd., "White Thermal Insulation Pigment Tipaque PFR404", retrieved on Apr. 7, 2023, 3 pages (with English Translation).
Kaoru Isobe, "Heat ray shielding material", Special Feature Heat, Publication 8_ Journal of the Society of Inorganic Materials, Japan 14, 2007, pp. 397-402 (with English Translation).

*Primary Examiner* — Susan T Tran
(74) *Attorney, Agent, or Firm* — Oblon, McClelland, Maier & Neustadt, L.L.P.

(57) ABSTRACT

[1] An external skin preparation for IR protection, an external skin preparation for heat insulation, an external skin preparation for photoaging prevention, an external preparation for skin temperature increase prevention, an external skin preparation for fatigue prevention and an external skin preparation for active oxygen production prevention, containing a tabular metal oxide (A) having a thickness of 30 to 360 nm, and [2] an external skin preparation containing a tabular metal oxide (A) having a thickness of 30 nm or more and 360 nm or less and an aspect ratio of 50 or more and 300 or less, and a nonvolatile oil (B) in a ratio by mass [(A)/(B)] of 0.05 to 5.

13 Claims, No Drawings

(56) References Cited

FOREIGN PATENT DOCUMENTS

| | | |
|---|---|---|
| JP | 2013-511515 A | 4/2013 |
| JP | 2017-95361 A | 6/2017 |
| JP | 2017-155006 A | 9/2017 |
| JP | 2017-171655 A | 9/2017 |
| JP | 2017-206484 A | 11/2017 |
| JP | 2019-6712 A | 1/2019 |
| KR | 10-2013-0105619 A | 9/2013 |
| KR | 10-2017-0114508 A | 10/2017 |
| KR | 10-2018-0110960 A | 10/2018 |
| WO | WO 2009/017104 A1 | 2/2009 |
| WO | WO 2017/175164 A1 | 10/2017 |
| WO | WO 2019/107304 A1 | 6/2019 |

* cited by examiner

EXTERNAL PREPARATION

CROSS REFERENCE TO RELATED APPLICATION

This application is a national stage entry under 35 USC 371 of PCT/JP2019/051469, filed on Dec. 27, 2019, and claims priority to PCT/JP2018/048006, filed on Dec. 27, 2018 and Japanese Patent Application No. 2018-244998 filed on Dec. 27, 2018.

FIELD OF THE INVENTION

The present invention relates to an external skin preparation for IR protection, an external skin preparation for heat insulation, an external skin preparation for photoaging prevention, an external preparation for skin temperature increase prevention, an external skin preparation for fatigue prevention, an external skin preparation for active oxygen production prevention, and an external skin preparation.

BACKGROUND OF THE INVENTION

From the viewpoint of protecting skin from sunlight, UV protective cosmetics such as sunblock cosmetics are known. On the other hand, with the recent increase in health consciousness, an external skin preparation having a protective function against IR rays has become desired.

Regarding such an external skin preparation having an IR protective function, for example, WO2009/017104 (Patent Literature 1) discloses a near-IR damage protective agent for body tissues, which contains an IR transmission masking agent of a titanium oxide powder and a zinc oxide powder, as a technique relating to an inhibitor that inhibits IR rays from reaching a tissue deeper than a skin tissue to thereby prevent the tissues from damage by IR rays.

Also, J P 2017-95361 A (Patent Literature 2) discloses a near IR protective cosmetic composition containing a titanium oxide powder and a zinc oxide powder, which satisfies both an excellent near IR protective effect and a high transparency.

SUMMARY OF THE INVENTION

The present invention relates to an external skin preparation for IR protection, an external skin preparation for heat insulation, an external skin preparation for photoaging prevention, an external preparation for skin temperature increase prevention, an external skin preparation for fatigue prevention, an external skin preparation for active oxygen production prevention and an external skin preparation, which contain a tabular metal oxide (A) having a thickness of 30 nm or more and 360 nm or less, and an aspect ratio of 50 or more and 300 or less.

DETAILED DESCRIPTION OF THE INVENTION

For skin protection, an external skin preparation capable of further improving an IR protective function than before and capable of realizing an actual sensation of higher-level heat insulation is awaited. In addition to this, an external skin preparation that can be readily spread on skin and can give good smoothness to the skin after application thereof is also desired.

Further, among external skin preparations, a skin cosmetic material is desired to hardly whiten when applied to skin to be able to give a natural appearance, and to secure a good adhesion of makeup to be able to give a good sense of use after applied to skin.

The present invention relates to various external preparations (I) excellent in an IR protective effect, capable of giving an actual sense of high-level heat insulation, excellent in spreadability on skin, and capable of giving good smoothness after applied to skin.

The present invention also relates to ab external skin preparation (II) excellent in an IR protective effect, which, when applied to skin, hardly whitens and can give a natural appearance, and which, after applied to skin, secures a good adhesion of makeup.

The present inventors have found that external preparations (I) containing a metal oxide having a predetermined shape are excellent in an IR protective effect and a heat insulative effect, can be readily spread on skin, and can secure good smoothness when applied to skin.

The present inventors have also found that an external skin preparation (II) containing a metal oxide having a predetermined shape and a nonvolatile oil in a predetermined ratio can solve the above-mentioned problems.

Specifically, the present invention relates to the following [1] to [4].

[1] An external skin preparation for IR protection, an external skin preparation for heat insulation, an external skin preparation for photoaging prevention, an external preparation for skin temperature increase prevention, an external skin preparation for fatigue prevention and an external skin preparation for active oxygen production prevention (I), containing a tabular metal oxide (A) having a thickness of 30 nm or more and 360 nm or less.

[2] An external skin preparation (II), containing a tabular metal oxide (A) having a thickness of 30 nm or more and 360 nm or less and an aspect ratio of 50 or more and 300 or less, and a nonvolatile oil (B) in a ratio by mass [(A)/(B)] of 0.05 or more and 5 or less.

[3] A method for protecting skin from IR ray, insulating skin from heat, protecting skin from photoaging, preventing skin temperature increase, preventing skin from being fatigued or preventing active oxygen production in skin, which includes applying the external skin preparation for IR protection, the external skin preparation for heat insulation, the external skin preparation for photoaging prevention, the external preparation for skin temperature increase prevention, the external skin preparation for fatigue prevention or the external skin preparation for active oxygen production prevention (I) of the above [1] to skin.

[4] A method for protecting skin from IR rays, which includes applying the external skin preparation (II) of the above [2] to skin.

The external preparations (I) of the present invention are excellent in an IR protective effect, can give an actual sense of high-level heat insulation, can be readily spread on skin, and can give good smoothness after applied to skin. By applying the external preparation of the present invention to skin, there can be achieved an effect of insulating skin from heat, an effect of protecting skin from photoaging, an effect of preventing skin temperature increase, an effect of preventing skin from being fatigued by irradiation with sunlight, and an effect of preventing active oxygen production in skin.

The external skin preparation (II) of the present invention is excellent in an IR protective effect and can give an actual sense of high-level heat insulation, and when applied to skin, it hardly whitens and can give a natural appearance, and after applied to skin, it secures a good adhesion of makeup and gives a good sense of use, and accordingly, the external skin preparation is useful, for example, as a skin cosmetic material.

[External Preparation]

The external preparations (I) of the present invention are an external skin preparation for IR protection, an external skin preparation for heat insulation, an external skin preparation for photoaging prevention, an external preparation for skin temperature increase prevention, an external skin preparation for fatigue prevention and an external skin preparation for active oxygen production prevention, containing a tabular metal oxide (A) having a thickness of 30 nm or more and 360 nm or less.

The external skin preparation (II) of the present invention contains a tabular metal oxide (A) having a thickness of 30 nm or more and 360 nm or less and an aspect ratio of 50 or more and 300 or less, and a nonvolatile oil (B) in a ratio by mass [(A)/(B)] of 0.05 or more and 5 or less.

In the following description, the above-mentioned various external preparations may be collectively called "external preparations".

In the present invention, the thickness of the tabular metal oxide means a length of the shortest axis in a tabular metal oxide particle.

Also in the present invention, IR rays mean electromagnetic waves having a wavelength of 780 nm to 1 mm. Among these, the external preparations of the present invention are especially excellent in an effect of protecting from near IR rays having a wavelength of 780 nm to 2500 nm. Accordingly, the external preparations of the present invention can prevent photoaging of skin by irradiation with sunlight, skin temperature increase, skin fatigue caused by irradiation with sunlight, and active oxygen production in skin, and can give a further higher heat insulative effect.

In this description, an IR protection factor at a wavelength of 1500 nm is used as an index for the IR protective effect.

The external preparations of the present invention are external preparations for protection from IR rays, heat insulation, photoaging preventing, skin temperature increase prevention, fatigue prevention and active oxygen production prevention, and are differentiated from an external skin preparation for UV protection that is contained in sunscreen cosmetic materials. Having an effect of IR protection, the external preparations of the present invention can prevent photoaging of skin (wrinkling, sagging) and skin temperature increase caused by irradiation with IR rays, or with sunlight that contains light having a wavelength falling within an IR range, and also skin fatigue and active oxygen production in skin caused by irradiation with sunlight, therefore providing a higher-level heat insulation effect. So far as having the above-mentioned effects, the external preparations of the present invention shall not be precluded from further having a UV protective effect.

The dosage form of the external preparations of the present invention is not specifically limited, but is, from the viewpoint of applicability to skin, preferably liquid, gel or cream. The external preparations may also be in a form of an emulsified composition, and the emulsified composition may be any of an oil-in-water type emulsified composition or a water-in-oil type emulsified composition.

The external skin preparations of the present invention may also be skin cosmetic materials such as lotion, cream, emulsion, serum, suntan agent or liquid foundation, in addition to external skin preparations for IR protection. Preferred are skin cosmetic materials, as hardly whitening and capable of giving a natural appearance when applied to skin, and as securing a good adhesion of makeup after applied to skin.

<Tabular Metal Oxide (A)>

The external preparations of the present invention contain a tabular metal oxide (A) having a thickness of 30 nm or more and 360 nm or less.

Containing such a tabular metal oxide having a predetermined thickness as the component (A), the external preparations of the present invention are excellent in an IR protective effect and can realize an actual sensation of high-level heat insulation, and in addition, when applied to skin, they are readily spread and can give a good smoothness. Further, the external preparations additionally have an effect of hardly whitening (transparency) when applied to skin, or an effect of hardly whitening to give a natural appearance.

It is known that an external skin preparation containing inorganic particles of titanium oxide or the like can have a higher IR protective effect when the inorganic particles therein have a large particle size. However, mere use of inorganic particles having a large particle size is limited in improving the IR protective effect. In addition, for example, in the case where spherical inorganic particles having a particle size larger than the wavelength of visible light are blended in an external skin preparation and when the external skin preparation is applied to skin, it may often whiten owing to visible light scattering on the surfaces of the particles therein, therefore providing a problem of giving a sense of inferiority in natural appearance. Consequently, when the particle size of the inorganic particles to be used is merely controlled, it is still difficult to satisfy both the IR protective effect and the transparency or the natural sense of appearance in applying the preparation to skin.

The present inventors have found that, when a tabular metal oxide having a predetermined thickness is used as the component (A) in an external preparation, it is possible to reduce the reflectance of light in a visible region while selectively increasing the reflectance of light in an IR region by the interference effect of light, and accordingly, it becomes possible to satisfy both the IR protective effect and the transparency.

When the thickness of the component (A) falls within the above-mentioned predetermined range (30 nm or more and 360 nm or less), and when an external preparation containing the component (A) is applied to skin, the reflectance of light to be observed on the side of the skin surface can be such that the reflectance of light having a wavelength in an IR region is high while that of light having a wavelength in a visible region is low owing to the interference effect of light. Consequently, the external preparations of the present invention can satisfy both a high IR protective effect and a transparency or a sense of natural appearance when applied to skin.

Using the above-mentioned predetermined component (A) also betters spreadability on skin and smoothness in applying to skin.

From the viewpoint of achieving an excellent IR protective effect and an actual sense of heat insulation owing to the above-mentioned mechanism of action, and from the viewpoint of spreadability on skin, smoothness and a sense of natural appearance when applied to skin, the thickness of the component (A) is 30 nm or more, preferably 50 nm or more, more preferably 60 nm or more, even more preferably 80 nm or more, further more preferably 105 nm or more, further more preferably 125 nm or more. Also from the same viewpoints, the thickness of the component (A) is 360 nm or less, preferably 330 nm or less, more preferably 310 nm or less, even more preferably 280 nm or less, further more preferably 270 nm or less, further more preferably 230 nm or less. A specific range of the thickness of the component (A) is preferably 50 nm or more and 330 nm or less, more preferably 60 nm or more and 310 nm or less, even more preferably 60 nm or more and 280 nm or less, further more preferably 80 nm or more and 280 nm or less, further more preferably 105 nm or more and 270 nm or less, further more preferably 125 nm or more and 270 nm or less, further more preferably 125 nm or more and 230 nm or less.

The thickness of the component (A) can be determined on an image observed with a scanning electronic microscope (SEM). Specifically, the component (A) is observed with SEM under the condition of an observation magnification of 10,000 times, the thickness of 50 particles in the observed image is measured individually, and the found data of the thickness are averaged to give an average of the thickness per number of particles. Specifically, the thickness of the component (A) can be measured according to the method described in the section of Examples.

From the viewpoint of achieving an excellent IR protective effect, and from the viewpoint of achieving spreadability on skin, smoothness and a sense of natural appearance when applied to skin, the aspect ratio of the component (A) is preferably 50 or more, more preferably 55 or more, even more preferably 65 or more, further more preferably 70 or more, and from the same viewpoints, the aspect ratio is preferably 300 or less, more preferably 230 or less, even more preferably 200 or less, further more preferably 140 or less, further more preferably 125 or less, further more preferably 120 or less. A specific range of the aspect ratio of the component (A) is, for example, 50 or more and 300 or less, preferably 50 or more and 230 or less, more preferably 55 or more and 230 or less, even more preferably 55 or more and 200 or less, further more preferably 55 or more and 140 or less, further more preferably 55 or more and 125 or less, further more preferably 65 or more and 125 or less, further more preferably 70 or more and 120 or less.

In the external skin preparation (II), the aspect ratio of the component (A) is 50 or more and 300 or less, and a preferred range thereof is as mentioned above.

The aspect ratio of the component (A) is determined as follows. Under the same condition as above, the particles are observed with SEM, the length of the shortest axis (thickness) and the length of the longest axis (long diameter) of 50 particles in the observed image are measured individually to calculate an aspect ratio (long diameter/thickness) of each particle, and the resultant data are averaged to give an average aspect ratio of the particles. Specifically, the aspect ratio of the tabular metal oxide can be measured according to the method described in the section of Examples.

The metal oxide of a high refractive index material to constitute the component (A) can realize a high light interference effect. From this viewpoint, a preferred metal oxide to constitute the component (A) is one or more selected from the group consisting of titanium oxide, zinc oxide, zirconium oxide, iron oxide, aluminum oxide, cerium oxide, etc. Among these, one or more selected from the group consisting of titanium oxide and zinc oxide are preferred, and titanium oxide is more preferred. Specifically, the component (A) is preferably one or more selected from tabular titanium oxide and tabular zinc oxide, more preferably tabular titanium oxide.

The crystal structure of titanium oxide may be any of a rutile type or an anatase type, or amorphous, but from the viewpoint of achieving an excellent IR protective effect and an actual sensation of high-level heat insulation, a rutile type is preferred.

The tabular metal oxide of the component (A) may be one not treated on the surface thereof, but for the purpose of enhancing the dispersibility thereof in the external preparation, it may be optionally surface-treated for hydrophobization or the like according to a known method. The tabular metal oxide of the component (A) is differentiated from those prepared by surface-treating any other particles than metal oxides with a metal oxide.

The surface-treating agent for use for surface treatment of the component (A) includes silicones; alkylalkoxysilanes; fluorine-containing compounds such as perfluoroalkyl phosphates, and perfluoroalcohols; amino acids such as N-acylglutamic acids; others such as lecithin; metal soaps; fatty acids such as stearic acid; alkyl phosphates, etc. Among these, from the viewpoint of enhancing the dispersibility of the component (A) in the external preparation, one or more selected from the group consisting of silicones and alkylalkoxysilanes are preferred.

Silicones as a surface-treating agent are not specifically limited, and examples thereof include various silicone oils such as methylpolysiloxane, dimethylpolysiloxane, methylphenylpolysiloxane, methylhydrogen polysiloxane, methylcyclopolysiloxane, octamethylcyclotetrasiloxane, decamethylcyclopentasiloxane, dodecamethylcyclohexasiloxane, octamethyltrisiloxane, tetradecamethylhexasiloxane, dimethylsiloxane-methyl(polyoxyethylene)siloxane-methyl (polyoxypropylene)silo xane copolymer, dimethylsiloxane-methyl(polyoxyethylene)siloxane copolymer, dimethylsiloxane-methyl(polyoxypropylene)siloxane copolymer, dimethylsiloxane-methylcetyloxysiloxane copolymer, dimethylsiloxane-methylstearoxysiloxane copolymer, and (alkyl acrylate/dimethicone) copolymer.

The alkylalkoxysilane as a surface-treating agent is preferably one having a linear or branched alkyl group having 6 to 20 carbon atoms, and is especially preferably octyltriethoxysilane or octyltrimethoxysilane.

From the viewpoint of improving the IR protective effect, one or more selected from the group consisting of methylpolysiloxane, dimethylpolysiloxane, methylhydrogen polysiloxane, (alkyl acrylate/dimethicone) copolymer and octyltriethoxysilane are preferred.

In the case where the component (A) is a surface-treated one, the coating amount with the surface-treating agent is, from the viewpoint of enhancing dispersibility in the external skin preparation, preferably 1% by mass or more and 9% by mass or less, more preferably 2% by mass or more and 8% by mass or less relative to the total amount of the tabular metal oxide of the component (A).

The content of the component (A) in the external preparations is, from the viewpoint of achieving an excellent IR protective effect and an actual sense of heat insulation, and from the viewpoint of achieving spreadability on skin, smoothness and a sense of natural appearance when applied to skin, preferably 1% by mass or more, more preferably 3% by mass or more, even more preferably 6% by mass or more, further more preferably 8% by mass or more, further more preferably 15% by mass or more, further more preferably 25% by mass or more. Also from the viewpoint of achieving spreadability on skin, smoothness and a sense of natural appearance when applied to skin, and from the viewpoint of a good adhesion of makeup after applied to skin, the content of the component (A) in the external preparations is preferably 35% by mass or less. From the viewpoint of achieving transparency and a sense of natural appearance when applied to skin, and from the viewpoint of reducing a feel of squeakiness, the content of the component (A) in the external preparations is preferably 25% by mass or less, more preferably 17% by mass or less, even more preferably 15% by mass or less, further more preferably 12% by mass or less.

A specific range of the content of the component (A) in the external skin preparation is, from the viewpoint of achieving an excellent IR protective effect, an excellent effect of heat insulation, spreadability on skin, smoothness and a sense of natural appearance when applied to skin, and a good adhesion of makeup after applied to skin, preferably 1% by mass or more and 35% by mass or less more preferably 3% by mass or more and 35% by mass or less, even more preferably 6% by mass or more and 35% by mass or less, further more preferably 8% by mass or more and 35% by mass or less, further more preferably 15% by mass or more and 35% by mass or less, further more preferably 25% by mass or more and 35% by mass or less. In addition to the above-mentioned viewpoints, also from the viewpoint of attaining transparency in applying to skin and reducing a feel of squeakiness of skin, the range is preferably 1% by mass or more and 35% by mass or less, more preferably 3% by mass or more and 25% by mass or less, even more preferably 6% by mass or more and 25% by mass or less, further more preferably 6% by mass or more and 17% by mass or less, further more preferably 6% by mass or more and 15% by mass or less, further more preferably 8% by mass or more and 15% by mass or less, further more preferably 8% by mass or more and 12% by mass or less.

As the component (A), commercial products of a tabular metal oxide can be used. For example, commercial products of tabular titanium oxide include "Featheleve PT-9001K", "Featheleve PT-7001K", "Featheleve PT-7401K", "Featheleve PT-7801K", and "Featheleve PT-7901K" from CQV Co., Ltd.

(Nonvolatile Oil (B))

The external skin preparation (II) of the present invention contains a nonvolatile oil (B) from the viewpoint of achieving an excellent IR protective effect and from the viewpoint of a sense of natural appearance when applied to skin and a good adhesion of makeup after applied to skin. The nonvolatile oil is such that the amount of evaporation thereof, as measured according to the method (1) mentioned below, is less than 20% at 25° C. for 6 hours.

Method (1): A piece of filter paper having a diameter of 90 mm is put in a glass laboratory dish having a diameter of 120 mm, 1 g of a sample is put on the filter paper, and stored in room (25° C.) at 65% RH. After 6 hours, the residue of the sample is measured, and the amount of evaporation thereof is calculated.

Also preferably, the component (B) is liquid under one atmospheric pressure at 25° C. More specifically, the viscosity at 25° C. of the component (B) is preferably 500 mPa·s or less, more preferably, 300 mPa·s or less, even more preferably 100 mPa·s or less, further more preferably 50 mPa·s or less, and is preferably 5 m Pa's or more.

The viscosity is measured using a B-type viscometer "TVB-10" (from Toki Sangyo Co., Ltd.) with a rotor No. 1, at 25° C. and 60 rpm for 1 minute.

Specifically, the component (B) is a nonvolatile oil liquid at 25° C., and examples thereof include one or more selected from the group consisting of an ester oil, a silicone oil, a hydrocarbon oil, a higher fatty acid, and a higher alcohol.

Examples of the nonvolatile liquid ester oil include one or more selected from the group consisting of isononyl isononanoate, isotridecyl isononanoate, isopropyl myristate, isocetyl myristate, octyldodecyl myristate, isopropyl palmitate, ethylhexyl palmitate, 2-hexyldecyl palmitate, glyceryl tri-2-ethylhexanoate, di-2-ethylhexyl sebacate, diisopropyl sebacate, glyceryl tri (caprylate/caprate), diisostearyl malate, diethylene glycol dicaprylate, neopentyl glycol dicaprate, neopentyl glycol dicaprate, neopentyl glycol di-2-ethylhexanoate, alkyl benzoates such as alkyl (C12 to C15) benzoates, etc.

Among the above, from the viewpoint of a sense of natural appearance when applied to skin, a good adhesion of makeup after applied to skin, and little stickiness, a monoester of a fatty acid having 12 or more and 18 or less carbon atoms and a branched alcohol having 2 or more and 22 or less carbon atoms, a triester of a branched fatty acid having 6 or more and 18 or less carbon atoms and glycerin, a diester of a dicarboxylic acid having 2 or more and 18 or less carbon atoms and a branched alcohol having 2 or more and 18 or less carbon atoms, a diester of a fatty acid having 6 or more and 18 or less carbon atoms and a branched dialcohol having 2 or more and 10 or less carbon atoms, an alkyl (C12 to C15) benzoate (e.g., Finsolv TN, by Innospec Active Chemicals LLC) and the like are preferred; and specifically, one or more selected from the group consisting of isopropyl myristate, isocetyl myristate, octyldodecyl myristate, isopropyl palmitate, ethylhexyl palmitate, 2-hexyldecyl palmitate, glyceryl tri-2-ethylhexanoate, diisopropyl sebacate, di-2-ethylhexyl sebacate, diisostearyl malate, neopentyl glycol di-2-ethylhexanoate, neopentyl glycol dicaprate, and alkyl (C12 to C15) benzoates are more preferred; and one or more selected from the group consisting of isopropyl palmitate and alkyl (C12 to C15) benzoates are even more preferred.

The nonvolatile liquid silicone oil is, from the viewpoint of suppressing stickiness when applied to skin, preferably a methylpolysiloxane, and more preferably a methylpolysiloxane having a viscosity at 25° C. of 20 mPa·s or less.

The nonvolatile liquid hydrocarbon oil includes liquid paraffin, light liquid isoparaffin such as hydrogenated polyisobutene, heavy liquid isoparaffin, liquid ozokerite, squalane, pristane, squalene, isohexadecane, etc. Among these, from the viewpoint of suppressing stickiness when applied to skin, one or more selected from the group consisting of light liquid isoparaffin and isohexadecane are preferred, and light fluid isoparaffin is more preferred.

The nonvolatile liquid higher fatty acid includes a fatty acid having 12 or more and 22 or less carbon atoms, specifically oleic acid, isostearic acid, linolic acid, linoleic acid, etc.

The nonvolatile liquid higher alcohol includes an alcohol having 12 or more and 28 or less carbon atoms, specifically oleyl alcohol, 2-decyl-tetradecanol, dodecanol, isostearyl alcohol, octyl dodecanol, etc.

Of the nonvolatile oil that is liquid at 25° C., the component (B) is, from the viewpoint of suppressing stickiness when applied to skin, preferably one or more selected from the group consisting of an ester oil, a silicone oil and a hydrocarbon oil, more preferably one or more selected from the group consisting of isopropyl palmitate, alkyl (C12-15) benzoates, methylpolysiloxane and light liquid isoparaffin, and even more preferably, contains methylpolysiloxane.

In the external skin preparation (II) of the present invention, the ratio by mass [(A)/(B)] is, from the viewpoint of achieving an excellent IR protective effect, and from the viewpoint of a sense of natural appearance when applied to skin and a good adhesion of makeup after applied to skin, preferably 0.05 or more, more preferably 0.1 or more, even more preferably 0.2 or more, further more preferably 0.26 or more, further more preferably 0.3 or more. Also the ratio by mass [(A)/(B)] is, from the viewpoint of a sense of natural appearance when applied to skin and a good adhesion of makeup after applied to skin, preferably 5 or less, more preferably 2 or less, even more preferably 0.75 or less, further more preferably 0.5 or less, further more preferably 0.45 or less. A specific range of the ratio by mass [(A)/(B)] in the external skin preparation (II) is, from the viewpoint of achieving an excellent IR protective effect, and from the viewpoint of satisfying both a sense of natural appearance when applied to skin and a good adhesion of makeup after applied to skin, preferably 0.05 or more and 5 or less, more preferably 0.1 or more and 2 or less, even more preferably 0.1 or more and 0.75 or less, further more preferably 0.2 or more and 0.5 or less, further more preferably 0.26 or more and 0.45 or less, further more preferably 0.3 or more and 0.45 or less.

The content of the component (B) in the external skin preparation (II) of the present invention is not specifically limited so far as the ratio by mass [(A)/(B)] could be 0.05 or more and 5 or less, but is, from the viewpoint of achieving an excellent IR protective effect, and from the viewpoint of a sense of natural appearance when applied to skin, and a good adhesion of makeup after applied to skin, preferably 1% by mass or more, more preferably 5% by mass or more, even more preferably 15% by mass or more, further more preferably 20% by mass or more, further more preferably 25% by mass or more, further more preferably 28% by mass or more, and is, from the viewpoint of achieving an excellent IR protective effect and a good adhesion of makeup after applied to skin, preferably 45% by mass or less, more preferably 38% by mass or less, even more preferably 35% by mass or less, further more preferably 32% by mass or less. A specific range of the content of the component (B) in the external skin preparation (II) is, from the viewpoint of achieving an excellent IR protective effect, and satisfying both a sense of natural appearance when applied to skin and a good adhesion of makeup after applied to skin, preferably 1% by mass or more and 15% by mass or less, more preferably 5% by mass or more and 15% by mass or less, even more preferably 15% by mass or more and 38% by mass or less, further more preferably 20% by mass or more and 38% by mass or less, further more preferably 25% by mass or more and 35% by mass or less, further more preferably 28% by mass or more and 32% by mass or less.

In the case where the external skin preparation (II) of the present invention is a water-in-oil type emulsion composition, the content of the component (B) therein is, from the viewpoint of securing the water-in-oil form thereof, preferably 10% by mass or more, more preferably 15% by mass or more, even more preferably 18% by mass or more. The upper limit of the content of the component (B) in the water-in-oil type emulsion composition is, from the viewpoint of emulsion stability, preferably 60% by mass or less, more preferably 40% by mass or less, even more preferably 30% by mass or less.

In the case where the external skin preparation (II) of the present invention is an oil-in-water type emulsion composition, the content of the component (B) therein is, from the viewpoint of securing the oil-in-water form thereof, preferably 30% by mass or less, more preferably 20% by mass or less, even more preferably 10% by mass or less. The lower limit of the content of the component (B) in the oil-in-water type emulsion composition is, from the viewpoint of emulsion stability, preferably 1% by mass or more, more preferably 3% by mass or more, even more preferably 5% by mass or more.

From the viewpoint of achieving an excellent IR protective effect and from the viewpoint of a sense of natural appearance when applied to skin and a good adhesion of makeup after applied to skin, the total content of the components (A) and (B) in the external skin preparation (II) is preferably 2% by mass or more, more preferably 10% by mass or more, even more preferably 20% by mass or more, further more preferably 30% by mass or more, further more preferably 35% by mass or more, and the upper limit thereof is 100% by mass.

(Volatile Oil (B)')

The external skin preparation (II) of the present invention may further contains a volatile oil as a component (B)'. The volatile oil is such that the amount of evaporation thereof, as measured according to the method (1) mentioned below, is 20% or more at 25° C. for 6 hours.

Method (1): A piece of filter paper having a diameter of 90 mm is put in a glass laboratory dish having a diameter of 120 mm, 1 g of a sample is put on the filter paper, and stored in room (25° C.) at 65% RH. After 6 hours, the residue of the sample is measured, and the amount of evaporation thereof is calculated.

The component (B)' is, from the viewpoint of suppressing stickiness when applied to skin, preferably a volatile silicone oil, more preferably a linear organopolysiloxane and a cyclic organopolysiloxane that are liquid and volatile at 25° C.

Specific examples of the linear organopolysiloxane include octamethyltrisiloxane, decamethyltetrasiloxane, dodeacmethylpentasiloxane, and 1,1,1,3,5,5,5-heptamethyl-3-[(trimethylsilyl)oxy]-trisiloxane.

The cyclic organopolysiloxane includes a 4- to 6-membered cyclic siloxane having an alkyl group with 1 or more and 5 or less carbon atoms as a substituent, and specific examples thereof include octamethylcyclotetrasiloxane and decamethylcyclopentasiloxane.

Among the above, the component (B)' is, from the viewpoint of little stickiness when applied to skin, preferably a cyclic organopolysiloxane, more preferably decamethylcyclopentasiloxane.

Commercial products of the volatile silicone oil usable as the component (B) include "KF-96A-1cs" (octamethyltrisiloxane), "KF-96L-1.5cs" (decamethyltetrasiloxane), "KF-96L-2cs" (dodecamethylpentasiloxane", "KF-995" (decamethylcyclopentasiloxane), and "TMF-1.5" (1,1,1,3,5,5,5-heptamethyl-3-[(trimethylsilyl)oxy]-trisiloxane) from Shin-Etsu Chemical Co., Ltd.; "SH200C Fluid 1cs" (octamethyltrisiloxane), "SH200C Fluid 1.5cs" (decamethyltetrasiloxane), "SH200C Fluid 2cs" (dodecamethylpentasiloxane), and "SH245 Fluid" (decamethylcyclopentasiloxane) from DuPont Toray Specialty Materials K.K.; and "TSF405" (decamethylcyclopentasiloxane) from Momentive Performance Materials Corporation.

In the case where the external skin preparation (II) of the present invention contains the component (B)', the content thereof is, from the viewpoint of achieving an excellent IR protective effect and an actual sense of heat insulation, and from the viewpoint of a sense of natural appearance when applied to skin, a good adhesion of makeup after applied to skin, and a stickiness preventive effect, preferably 5% by mass or more, more preferably 10% by mass or more, even more preferably 20% by mass or more, and is preferably 75% by mass or less, more preferably 60% by mass or less, even more preferably 40% by mass or less. A specific range of the content of the component (B)' in the external skin preparation (II) is preferably 5% by mass or more and 75% by mass or less, more preferably 10% by mass or more and 60% by mass or less, even more preferably 20% by mass or more and 40% by mass or less.

(Surfactant (C))

Preferably, the external skin preparation (II) of the present invention further contain a surfactant (C), from the viewpoint of satisfying both an IR protective effect, and a sense of natural appearance when applied to skin, and from the viewpoint of dispersing oily components in water or dispersing water-soluble components in oil.

As the component (C), a known surfactant is employable, and examples thereof include an anionic surfactant, a cationic surfactant, an ampholytic surfactant and a nonionic surfactant. In addition, a fluorine-based surfactant and a silicone-based surfactant are also employable.

Preferably, the external skin preparation (II) of the present invention contain at least a silicone-based surfactant from the viewpoint of satisfying both an IR protective effect and a sense of natural appearance when applied to skin, and from the viewpoint of dispersing oily components in water or dispersing water-soluble components in oil, more preferably a nonionic silicone-based surfactant.

Examples of the silicone-based surfactant include polyether-modified silicones represented by the following general formulae (1) to (3):

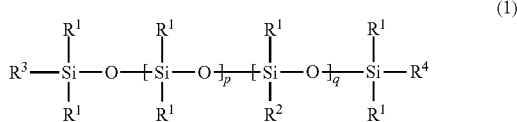
(1)

wherein $R^1$ represents an alkyl group having 1 or more and 5 or less carbon atoms, or a phenyl group; $R^2$ represents a group represented by a formula —$(CH_2)_r$—O—$(C_2H_4O)_s$—$(C_3H_6O)_t$—$R^5$ (where $R^5$ represents a hydrogen atom or an alkyl group having 1 or more and 5 or less carbon atoms, r represents a number of 1 or more and 5 or less, s represents a number of 1 or more and 50 or less, t represents a number of 0 or more and 30 or less); $R^3$ and $R^4$ each represent the same group as any one of $R^1$ or $R^2$; p represents a number of 5 or more and 300 or less; q represents a number of 1 or more and 50 or less; provided that all $R^1$'s are not to be a phenyl group.

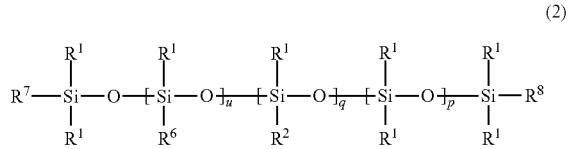
(2)

wherein $R^1$, $R^2$, p and q are the same as above; $R^6$ represents an alkyl group having 2 or more and 20 or less carbon atoms; $R^7$ and $R^8$ each represent the same group as any one of $R^1$, $R^2$ or $R^6$; u represents a number of 1 or more and 30 or less; provided that all $R^1$'s are not to be a phenyl group.

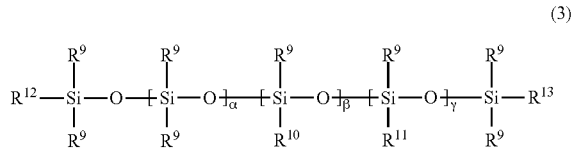
(3)

wherein $R^9$ represents an alkyl group having 1 or more and 4 or less carbon atoms; $R^{10}$ represents a group represented by a formula -$Q^1$-O—$(C_2H_4O)_x$—$(C_3H_6O)_y R^{14}$ (where $Q^1$ represents a divalent hydrocarbon group having 1 or more and 4 or less carbon atoms; $R^{14}$ represents a hydrogen atom, an alkyl group having 1 or more and 4 or less carbon atoms, or an acetyl group; x represents a number of 1 or more; y represents a number of 0 or more); $R^{11}$ represents a group represented by a formula -$Q^2$-O—$R^{15}$ (where $Q^2$ represents a divalent hydrocarbon group having 1 or more and 4 or less carbon atoms; $R^{15}$ represents a hydrocarbon group having 8 or more and 30 or less carbon atoms); $R^{12}$ and $R^{13}$ each represent the same group as any one of $R^9$, $R^{10}$ or $R^{11}$; α represents a number of 0 or more; β and γ each represent a number of 1 or more.

In the polyether-modified silicone represented by the general formulae (1) to (3), the silicone chain can have a branched structure, or the silicone can be co-modified with any other functional group than polyether, within a range not overstepping the intended purpose.

Examples of commercial products of the polyether-modified silicone represented by the general formula (1) include "KF-6015" and "KF-6017" from Shin-Etsu Chemical Co., Ltd.; "SH3775M" (polyoxyethylene/methylpolysiloxane copolymer) and "SH3772C" from DuPont Toray Specialty Materials K.K. The polyether-modified silicone represented by the general formula (2) includes a so-called alkylpolyether-modified silicone, and examples of commercial products thereof include "Abil WE-09" from Goldschmidt AG; and "KF-6038" from Shin-Etsu Chemical Co., Ltd. The polyether-modified silicone represented by the general formula (3) includes a polyoxyalkylene alkyl ether-co-modified organopolysiloxane, which can be readily produced by co-modifying a methylhydrogen polysiloxane with a polyoxyalkylene allyl ether and an allyl alkyl ether.

A partially-crosslinked polyether-modified silicone can also be used as a silicone-based surfactant. Such a partially-crosslinked polyether-modified silicone is one prepared by addition polymerization of an organohydrogen polysiloxane and an aliphatic unsaturated group-containing compound, and examples thereof are described in JP 4-272932 A and JP 5-140320 A.

The partially crosslinked polyether-modified organopolysiloxane polymer is a polymer composed of, as essential components, a component of the following general formula (4) and/or a component of the following general formula (a), in a combination of an organohydrogen polysiloxane represented by the following general formula (4):

(4)

wherein $R^{16}$ represents an alkyl group, an aryl group, an aralkyl group or a halogenohydrocarbon group optionally having a substituent having 1 or more and 18 or less carbon atoms; $R^{17}$ represents a polyoxyalkylene group represented by a formula —$C_nH_{2n}O(C_2H_4O)_d(C_3H_6O)_e R^{18}$ (where $R^{18}$ represents a hydrogen atom, a saturated aliphatic hydrocarbon group having 1 or more and 10 or less carbon atoms, or a monovalent group represented by —C(O)—$R^{19}$ (where $R^{19}$ represents a saturated aliphatic hydrocarbon group having 1 or more and 5 or less carbon atoms), d represents a number of 2 or more and 200 or less, e represents a number of 0 or more and 200 or less, d+e is a number of 3 or more and 200 or less, n represents a number of 2 or more and 6 or less), a is 1≤a≤2.5, b is 0.001≤b≤1, c is 0.001≤c≤1; and/or an organohydrogen polysiloxane represented by the following general formula (5):

(5)

wherein $R^{16}$ is the same as above, f is 1≤f≤3, g is 0.001≤g≤1.5; and a polyoxyalkylene represented by the following general formula (a):

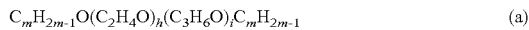

$$C_mH_{2m-1}O(C_2H_4O)_h(C_3H_6O)_iC_mH_{2m-1} \quad (a)$$

wherein h represents a number of 2 or more and 200 or less, i represents a number of 0 or more and 200 or less, h+i is a number of 3 or more and 200 or less, m represents a number of 2 or more and 6 or less; and/or an organopolysiloxane represented by the following general formula (b):

$$R^{16}{}_jR^{20}{}_kSiO_{(4-j-k)/2} \quad (b)$$

wherein $R^{16}$ is the same as above, $R^{20}$ represents a monovalent hydrocarbon having 2 or more and 10 or less carbon atoms and having an aliphatic unsaturated group at the terminal, j is 1≤j≤3, k is 0.001≤k≤1.5.

The other surfactant than the silicone-based surfactant is preferably a nonionic surfactant, more preferably a polyoxyethylene alkyl ether-based nonionic surfactant. Examples of commercial products of the nonionic surfactant include "Emulgen 121-G" (polyoxyethylene(21) lauryl ether) from Kao Corporation, "Emulgen 1620G" (polyoxyethylene(20) 2-hexyldecyl ether) from Kao Corporation, and "Emulgen 2020G" (polyoxyethylene(20) octyldodecyl ether) from Kao Corporation.

As the component (C), one or more kinds can be used either singly or as combined. Among the above, the component (C) is preferably one or more silicone-based surfactants selected from the group consisting of polyether-modified silicones represented by the general formulae (1) to (3), more preferably a silicone-modified surfactant of a polyether-modified silicone represented by the general formula (1).

In the case where the external skin preparation (II) of the present invention contains the component (C), the content thereof is, from the viewpoint of satisfying both an IR protective effect, and a sense of natural appearance when applied to skin, and from the viewpoint of dispersing oily components in water or dispersing water-soluble components in oil, preferably 0.1% by mass or more, more preferably 0.3% by mass or more, even more preferably 0.5% by mass or more, and is preferably 15% by mass or less, more preferably 10% by mass or less, even more preferably 5% by mass or less, further more preferably 1.5% by mass or less. A specific range of the content of the component (C) in the external skin preparation (II) of the present invention is preferably 0.1% by mass or more and 15% by mass or less, more preferably 0.3% by mass or more and 10% by mass or less, even more preferably 0.3% by mass or more and 5% by mass or less, further more preferably 0.5% by mass or more and 1.5% by mass or less.

(Aqueous Medium)

The external preparations of the present invention may further contain an aqueous medium from the viewpoint of dispersing the component (A) and dispersing or dissolving other formulation ingredients to improve applicability to skin. The aqueous medium is not specifically limited so far as it can disperse or dissolve the component (A) and other formulation ingredients, and examples thereof include water; a monoalcohol having 4 or less carbon atoms such as ethanol, isopropyl alcohol and butyl alcohol; and a low-molecular diol or triol having 6 or less carbon atoms such as 1,3-butylene glycol, glycerin, ethylene glycol, propylene glycol, diethylene glycol, and dipropylene glycol. Among these, one or more selected from the group consisting of water and a monoalcohol having 4 or less carbon atoms are preferred, and one or two selected from the group consisting of water and ethanol are more preferred.

The content of the aqueous medium in the external skin preparation (II) can be appropriately selected depending on the form of the external skin preparation (II), and is preferably 1% by mass or more, more preferably 5% by mass or more, even more preferably 8% by mass or more, further more preferably 10% by mass or more, and preferably 98% by mass or less, more preferably 90% by mass or less, even more preferably 70% by mass or less, further more preferably 50% by mass or less.

A specific range of the content of the aqueous medium in the external skin preparation (II) is preferably 1% by mass or more and 98% by mass or less, more preferably 5% by mass or more and 98% by mass or less, even more preferably 8% by mass or more and 90% by mass or less, further more preferably 10% by mass or more and 70% by mass or less, further more preferably 10% by mass or more and 50% by mass or less.

<Other Components>

The external preparations of the present invention can contain, as needed, any other component than the above-mentioned component (A), for example, a UV absorbent, a UV scattering agent, an oily agent, an emulsifier, an oil gelling agent, an antiperspirant, a fragrance, a moisturizer, a tackifier, a germicide, a pH regulator, an antioxidant, a preservative, etc.

(UV Absorbent)

The external preparations of the present invention can further contain a UV absorbent from the viewpoint of imparting a UV protective effect thereto.

The UV absorbent is preferably an organic UV absorbent except the components (B) and (B)', and can be an oil-soluble organic UV absorbent or a water-soluble organic UV absorbent. From the viewpoint of achieving a UV protective effect, a sense of natural appearance when applied to skin and a good adhesion of makeup after applied to skin, and from the viewpoint of suppressing stickiness, the UV absorbent is preferably an oil-soluble organic UV absorbent. "Oil-soluble" means a solubility in water of 1 w/w % or less.

From the viewpoint of achieving the advantageous effects of the present invention, preferably, the UV absorbent does not contain an inorganic UV absorbent such as a UV absorbent prepared by coating the surface of an inorganic filler with a UV absorbent material.

The usable oil-soluble organic UV absorbent includes oil-soluble ones of a salicylate-based UV absorbent, a cinnamate-based UV absorbent, a benzoylmethane-based UV absorbent, and other organic UV absorbents.

Examples thereof include:
a salicylate-based UV absorbent such as homomenthyl salicylate, and octyl salicylate;
a cinnamate-based UV absorbent such as 2-ethylhexyl p-methoxycinnamate (e.g., "Uvinul MC80" by BASF SE), glyceryl di-p-methoxycinnamate mono-2-ethylhexanoate, methyl 2,5-diisopropylcinnamate, methyl-bis(trimethylsiloxy)silylisopentyl trimethoxycinnamate, and isopropyl p-methoxycinnamate/diisopropylcinnamate mixture;
a benzoylmethane-based UV absorbent such as 4-isopropyldibenzoylmethane, and 4-tert-butyl-4'-methoxydibenzoylmethane (e.g., "Parasol 1789" by DSM Nutrition Japan K.K.);
octocrylene (e.g., "Parasol 340" by DSM Nutrition Japan K.K.), 2-ethylhexyl dimethoxybenzylidene dioxoimidazolidinepropionate (e.g., "Softshade DH" by Ajinomoto Co., Inc.), 1-(3,4-dimethoxyphenyl)-4,4-dimethyl-1,3-pentanedione, cinoxate, methyl O-aminobenzoate, 3-(4-methylbenzylidene) camphor, octyltriazone, hexyl diethylaminohydroxybenzoyl benzoate (hexyl (2-(4-diethylamino-2-hydroxybenzoyl) benzoate, e.g., "Uvinul A Plus" by BASF SE), bis-ethylhexyloxyphenol methoxyphenyl triazine (2,4-bis{[4-(2-ethylhexyloxy)-2-hydroxy] phenyl}-6-(4-methoxyphenyl)-1,3,5-triazin e, e.g., "Tinosorb by S" BASF SE), methylene bis-benzotriazolyl tetramethyl-butylphenol (e.g., "Tinosorb M" by BASF SE), and 2,1,6-tris [4-(2-ethylhexyloxycarbonyl)anilino]-1,3,5-triazine (hereinafter also referred to as "ethylhexyltriazone", e.g., "Uvinul T150" by BASF SE).

The usable water-soluble organic UV absorbent includes those having a solubility in water more than 1 w/w % of a salicylate-based UV absorbent, a cinnamate-based UV absorbent, a benzoylmethane-based UV absorbent and other organic UV absorbents, and examples thereof include triethanolamine salicylate, and diethanolamine p-methoxyhydrocinnamate.

Among the above, from the viewpoint of the UV protective effect thereof, the UV absorbent (B) is preferably one or more selected from the group consisting of 2-ethylhexyl p-methoxycinnamate, 4-tert-butyl-4'-methoxydibenzoylmethane, octocrylene, 2-ethylhexyl dimethoxybenzylidene dioxoimidazolidine propionate, hexyl diethylaminohydroxybenzoyl benzoate, bis-ethylhexyloxyphenol methoxyphenyl triazine, methylene bis-benzotriazolyl tetramethyl-butylphenol, and 2,4,6-tris [4-(2-ethylhexyloxycarbonyl) anilino]-1,3,5-triazine, more preferably one or more selected from the group consisting of 2-ethylhexyl p-methoxycinnamate, hexyl diethylaminohydroxybenzoyl benzoate, bis-ethylhexyloxyphenol methoxyphenyl triazine, and 2,4,6-tris [4-(2-ethylhexyloxycarbonyl)anilino]-1,3,5-triazine, and from the viewpoint of protecting from both UVA and UVB, even more preferably, two or more of these are combined. One or more selected from the group consisting of 2-ethylhexyl p-methoxycinnamate, hexyl diethylaminohydroxybenzoyl benzoate, and bis-ethylhexyloxyphenol methoxyphenyl triazine are further more preferred, and still further more preferably, two or more of these are combined.

In the case where the external preparations contain a UV absorbent, the content thereof is, from the viewpoint of a UV protective effect, preferably 0.2% by mass or more in the external preparation, more preferably 1.5% by mass or more, even more preferably 5% by mass or more, further more preferably 7% by mass or more. Also from the viewpoint of achieving an excellent IR protective effect and from the viewpoint of a good adhesion of makeup after applied to skin, the content is preferably 30% by mass or less, more preferably 25% by mass or less, even more preferably 20% by mass or less, further more preferably 15% by mass or less. A specific range of the content of the UV absorbent in the external preparations is, from the viewpoint of satisfying both an IR protective effect, and a good adhesion of makeup after applied to skin and a UV protective effect, preferably 0.2% by mass or more and 30% by mass or less, more preferably 1.5% by mass or more and 25% by mass or less, even more preferably 5% by mass or more and 20% by mass or less, further more preferably 7% by mass or more and 15% by mass or less.

(UV Scattering Agent)

The external preparations of the present invention may further contain a UV scattering agent from the viewpoint of achieving a UV protective effect.

The UV scattering agent is preferably inorganic particles as highly effective in scattering UV rays, and is more preferably metal oxide particles except the component (A). The metal oxide particles include titanium oxide, zinc oxide, iron oxide, zirconium oxide and aluminum oxide except the component (A), and are preferably those of one or more kinds selected from the group consisting of titanium oxide and zinc oxide except the component (A).

The inorganic particles for use for the UV scattering agent are, from the viewpoint of dispersibility in the external preparations, preferably those hydrophobized by surface treatment. Examples of surface treatment for hydrophobization include silicone treatment with methylhydrogen polysiloxane (hydrogen dimethicone), methylpolysiloxane (dimethicone), a methylhydrogen polysiloxane-dimethylpolysiloxane copolymer, etc.; fluorine treatment with a perfluoroalkyl phosphate, a perfluoroalcohol, etc.; amino acid treatment with an N-acylglutamic acid, etc.; silane compound treatment with hexyltrimethoxysilane, octyltrimethoxysilane, decyltrimethoxysilane, octadecyltrimethoxysilane, octyltriethoxysilane, trifluoropropyltrimethoxysilane, heptadecafluorodecyltrimethoxysilane, etc.; silazane treatment with hexamethyldisilazane, octyldisilazane, etc.; lecithin treatment; metal soap treatment; fatty acid treatment with caprylic acid, pelargonic acid, capric acid, lauric acid, myristic acid, palmitic acid, stearic acid, oleic acid, linolic acid, linolenic acid, arachic acid, arachidonic acid, behenic acid, etc.; alkyl phosphate treatment; and inorganic compound treatment with silica, alumina, aluminum hydroxide, etc. One or more kinds of such surface treatment methods can be employed.

The shape of the particles of the UV scattering agent may be spherical, rod-shaped, spindle-shaped, acicular, tabular or amorphous, and is not specifically limited so far as the particles achieve a UV scattering effect.

The number-average particle diameter of the UV scattering agent is generally 1 nm or more, and is, from the viewpoint of achieving an excellent UV protective effect, preferably 5 nm or more, more preferably 8 nm or more, even more preferably 10 nm or more. Also from the viewpoint of a sense of natural appearance when applied to skin, it is preferably 500 nm or less, more preferably 300 nm or less even more preferably 100 nm or less, further more preferably 60 nm or less.

The number-average particle diameter is determined by measuring the largest minor axis of each of 300 particles in an image taken with a transmission electron microscope (TEM) under the condition of 100,000 magnifications and averaging the resultant data to give an average value. Here, the largest minor axis means a minor axis having a largest diameter that crosses a major axis of a particle at right angles.

The UV scattering agent for use herein may be commercial products. Examples of commercial products of titanium oxide particles usable as the UV scattering agent except the component (A) include "MT-100TV" (aluminum hydroxide, treated with stearic acid) and "MTY-110M3S" (aluminum hydroxide, treated with silica and hydrogen dimethicone) from TAYCA Corporation.

Examples of commercial products of zinc oxide particles for use as the UV scattering agent except the component (A) include "FINEX-50-LPTM" (treated with dimethicone), "FINEX-25" (with no surface treatment) and "FINEX-25LP" (treated with dimethicone) from Sakai Chemical Industry Co., Ltd., and "MZ-300" (with no surface treatment), "MZ-504R3M" (treated with hydrogen dimethicone), "MZY-303S" (treated with hydrogen dimethicone), "MZ-306X" (treated with triethoxysilylethyl polydimethylsiloxyethyl hexyl dimethicone), "MZ-200" (with no surface treatment), "MZY-203S" (treated with hydrogen dimethicone", "MZ-150" (with no surface treatment), "MZY-153S" (treated with hydrogen dimethicone), "MZ-505S" and "MZY-505S" from TAYCA Corporation.

One alone or two or more kinds of the UV scattering agents can be used either singly or as combined.

In the case where the external preparations of the present invention contain a UV scattering agent, the content thereof is, from the viewpoint of a UV protective effect, preferably 1% by mass or more, more preferably 3% by mass or more, even more preferably 5% by mass or more. Also from the viewpoint of achieving spreadability on skin and smoothness in applying to skin, the content is preferably 20% by mass or less, more preferably 18% by mass or less, even more preferably 15% by mass or less. A specific range of the content of the UV scattering agent in the external agents is preferably 1% by mass or more and 20% by mass or less, more preferably 3% by mass or more and 18% by mass or less, even more preferably 5% by mass or more and 15% by mass or less.

(Production Method for External Preparations)

A production method for the external preparations of the present invention is not specifically limited, and depending on the form of the external preparations, any known method can be appropriately employed. For example, employable is a method of blending the component (A) and the other components and uniformly mixing them with a disperser or the like. In the case where an aqueous medium is used, also employable is a method of blending all the components except the aqueous medium and uniformly mixing them with a disperser or the like, and thereafter adding an aqueous medium and further stirring and mixing them with a homogenizer or the like.

In the case where the external preparations are water-in-oil emulsion compositions or oil-in-water emulsion compositions, an aqueous phase and an oily phase are separately prepared, and the two may be mixed.

[IR Protection Method, Heat Insulation Method, Photoaging Prevention Method, Skin Temperature Increase Prevention Method, Sunlight Exposure-Caused Fatigue Prevention Method, Active Oxygen Production Prevention Method for Skin]

The present invention also provides a method for protecting skin from IR ray, a method of insulating skin from heat, a method of protecting skin from photoaging, a method of preventing skin temperature increase, a method of preventing skin from being fatigued by exposure to sunlight, and a method of preventing active oxygen production in skin, which include applying the IR protective external skin preparation of the present invention to skin. The methods of the present invention are not specifically limited so far as they include a step of applying the external preparation (I) of the present invention to skin.

By applying the external preparation (I) of the present invention to skin, the skin can be effectively protected from irradiation with IR rays or with light having a wavelength in a IR range such as sunlight. Accordingly, photoaging of skin and skin temperature increase caused by irradiation with IR rays or with light including an IR wavelength range such as sunlight can be prevented, and a heat insulation effect for skin can be achieved.

When animals including humans carry out an endurance performance under sunlight exposure environments, they may be fatigued when the sunlight exposure dose is large, but according to the method using the external preparation (I) of the present invention, skin fatigue to be caused by such sunlight exposure can be prevented. Further, according to the method using the external preparation (I) of the present invention, active oxygen production in skin to be caused by exposure to IR rays or light including an IR wavelength range such as sunlight can be prevented.

In the method using the external preparation (I) of the present invention, the IR protection factor at a wavelength of 1500 nm is preferably 25% or more, more preferably 40% or more, even more preferably 45% or more, further more preferably 50% or more. An IR protection factor at a wavelength of 1500 nm of 25% or more, preferably 40% or more gives an actual sense of high-level heat insulation.

The IR protection factor (%) is a value represented by 100−X (%) in which X (%) means an IR transmissivity measured with a spectrophotometer, and specifically, it is measured according to the method described in the section of Examples.

[IR Protecting Method for Skin]

The present invention also provides an IR protecting method for skin, including applying the external skin preparation (II) of the present invention to skin. The IR protecting method of the present invention is not specifically limited so far as the method includes a step of applying the external skin preparation (II) of the present invention to skin.

In the IR protecting method using the external skin preparation (II) of the present invention, the IR protection factor at a wavelength of 1500 nm is preferably 10% or more, more preferably 12% or more, even more preferably 15% or more. When the IR protection factor at a wavelength of 1500 nm is 10% or more, the external skin preparation can realize an actual sensation of high-level heat insulation.

The IR protection factor (%) is a value represented by 100−X (%) in which X (%) means an IR transmissivity measured with a spectrophotometer, and specifically, it is measured according to the method described in the section of Examples.

Regarding the above-mentioned embodiments, the present invention further discloses the following embodiments.

<1>

One or more external preparations selected from the group consisting of an external skin preparation for IR protection, an external skin preparation for heat insulation, an external skin preparation for photoaging prevention, an external preparation for skin temperature increase prevention, an external skin preparation for fatigue prevention and an external skin preparation for active oxygen production prevention, containing a tabular metal oxide (A) having a thickness of 30 nm or more and 360 nm or less.

<2>

An external skin preparation, containing a tabular metal oxide (A) having a thickness of 30 nm or more and 360 nm or less and an aspect ratio of 50 or more and 300 or less, and a nonvolatile oil (B) in a ratio by mass [(A)/(B)] of 0.05 or more and 5 or less.

<3>

The external preparation according to <1> or <2>, wherein the thickness of the component (A) is preferably 50 nm or more, more preferably 60 nm or more, even more preferably 80 nm or more, further more preferably 105 nm or more, further more preferably 125 nm or more, and is preferably 330 nm or less, more preferably 310 nm or less, even more preferably 280 nm or less, further more preferably 270 nm or less, further more preferably 230 nm or less.

<4>

The external preparation according to any one of <1> to <3>, wherein the aspect ratio of the component (A) is preferably 50 or more, more preferably 55 or more, even more preferably 65 or more, further more preferably 70 or more, and is preferably 300 or less, more preferably 230 or less, even more preferably 200 or less, further more preferably 140 or less, further more preferably 125 or less, further more preferably 120 or less.

<5>
The external preparation according to any one of <1> to <4>, wherein the metal oxide constituting the component (A) is preferably one or more selected from the group consisting of titanium oxide, zinc oxide, zirconium oxide, iron oxide, aluminum oxide and cerium oxide, more preferably one or more selected from the group consisting of titanium oxide and zinc oxide, even more preferably titanium oxide.

<6>
The external preparation according to any one of <1> to <5>, wherein the content of the component (A) is preferably 1% by mass or more and 35% by mass or less, more preferably 3% by mass or more and 35% by mass or less, even more preferably 6% by mass or more and 35% by mass or less, further more preferably 8% by mass or more and 35% by mass or less, further more preferably 15% by mass or more and 35% by mass or less, further more preferably 25% by mass or more and 35% by mass or less.

<7>
The external preparation according to any one of <1> to <5>, wherein the content of the component (A) is preferably 1% by mass or more and 35% by mass or less, more preferably 3% by mass or more and 25% by mass or less, even more preferably 6% by mass or more and 25% by mass or less, further more preferably 6% by mass or more and 17% by mass or less, further more preferably 6% by mass or more and 15% by mass or less, further more preferably 8% by mass or more and 15% by mass or less, further more preferably 8% by mass or more and 12% by mass or less.

<8>
The external skin preparation according to any one of <2> to <7>, wherein the component (B) is one or more selected from the group consisting of an ester oil, a silicone oil, a hydrocarbon oil, a higher fatty acid, and a higher alcohol, preferably one or more selected from the group consisting of an ester oil, a silicone oil and a hydrocarbon oil, more preferably one or more selected from the group consisting of isopropyl palmitate, alkyl (C12-C15) benzoate, methylpolysiloxane, and light liquid isoparaffin, and even more preferably contains methylpolysiloxane.

<9>
The external skin preparation according to any one of <2> to <8>, wherein the content of the component (B) is preferably 1% by mass or more, more preferably 5% by mass or more, even more preferably 15% by mass or more, further more preferably 20% by mass or more, further more preferably 25% by mass or more, and is preferably 45% by mass or less, more preferably 38% by mass or less, even more preferably 35% by mass or less, further more preferably 32% by mass or less.

<10>
The external skin preparation according to any one of <2> to <9>, which is a water-in-oil type emulsion composition and in which the content of the component (B) is preferably 10% by mass or more, more preferably 15% by mass or more, even more preferably 18% by mass or more, and is preferably 60% by mass or less, more preferably 40% by mass or less, even more preferably 30% by mass or less.

<11>
The external skin preparation according to any one of <2> to <10>, which is an oil-in-water type emulsion composition and in which the content of the component (B) is preferably 30% by mass or less, more preferably 20% by mass or less, even more preferably 10% by mass or less, and is preferably 1% by mass or more, more preferably 3% by mass or more, even more preferably 5% by mass or more.

<12>
The external skin preparation according to any one of <2> to <11>, wherein the total content of the components (A) and (B) is preferably 2% by mass or more, more preferably 10% by mass or more, even more preferably 20% by mass or more, further more preferably 30% by mass or more, further more preferably 35% by mass or more, and is 100% by mass or less.

<13>
The external skin preparation according to any one of <2> to <12>, further containing a volatile oil (B)' whose content is preferably 5% by mass or more, more preferably 10% by mass or more, even more preferably 20% by mass or more, and is preferably 75% by mass or less, more preferably 60% by mass or less, even more preferably 40% by mass or less.

<14>
The external skin preparation according to <13>, wherein the component (B)' is a volatile silicone oil, preferably one or more selected from the group consisting of a linear organopolysiloxane and a cyclic organopolysiloxane, more preferably a cyclic organopolysiloxane, even more preferably a decamethylcyclopentasiloxane.

<15>
The external skin preparation according to any one of <2> to <14>, further containing a surfactant (C) whose content is preferably 0.1% by mass or more, more preferably 0.3% by mass or more, even more preferably 0.5% by mass or more, and is preferably 15% by mass or less, more preferably 10% by mass or less, even more preferably 5% by mass or less, further more preferably 1.5% by mass or less.

<16>
The external skin preparation according to <15>, wherein the component (C) contains at least a silicone-based surfactant, and preferably contains a nonionic silicone-based surfactant.

<17>
The external preparation according to any one of <1> to <16>, further containing an aqueous medium.

<18>
One or more external preparations selected from the group consisting of an external skin preparation for IR protection, an external skin preparation for heat insulation, an external skin preparation for photoaging prevention, an external preparation for skin temperature increase prevention, an external skin preparation for fatigue prevention and an external skin preparation for active oxygen production prevention, containing one or more tabular metal oxides (A) selected from tabular titanium oxide and tabular zinc oxide having a thickness of 80 nm or more and 280 nm or less whose content is 8% by mass or more and 35% by mass or less.

<19>
The external preparation according to <17>, wherein the aspect ratio of the component (A) is preferably 50 or more and 230 or less, more preferably 55 or more and 230 or less, even more preferably 55 or more and 200 or less, further more preferably 55 or more and 140 or less, further more preferably 55 or more and 125 or less, further more preferably 65 or more and 125 or less, further more preferably 70 or more and 120 or less.

<20>

The external preparation according to <18> or <19>, wherein the thickness of the component (A) is preferably 105 nm or more and 230 nm or less, more preferably 125 nm or more and 230 nm or less.

<21>

An external skin preparation containing one or more tabular metal oxides (A) selected from the group consisting of tabular titanium oxide and tabular zinc oxide having a thickness of 80 nm or more and 280 nm or less, and a nonvolatile oil (B) in a ratio by mass [(A)/(B)] of 0.2 or more and 5 or less.

<22>

An external skin preparation containing one or more tabular metal oxides (A) selected from the group consisting of tabular titanium oxide and tabular zinc oxide having a thickness of 80 nm or more and 280 nm or less, and a nonvolatile oil (B), wherein the content of the component (B) is 15% by mass or more and 38% by mass or less, and the ratio by mass [(A)/(B)] is 0.2 or more and 0.5 or less.

<23>

The external skin preparation according to any one of <2> to <17>, <21> and <22>, which is a skin cosmetic material.

<24>

An IR protecting method for skin, including applying the external preparation of any one of <1>, <3> to <7> and <17> to <20> to skin.

<25>

A heat insulating method for skin, including applying the external preparation of any one of <1>, <3> to <7> and <17> to <20> to skin.

<26>

A photoaging preventing method for skin, including applying the external preparation of any one of <1>, <3> to <7> and <17> to <20> to skin.

<27>

A skin temperature increase preventing method, including applying the external preparation of any one of <1>, <3> to <7> and <17> to <20> to skin.

<28>

A fatigue preventing method for skin caused by exposure to sunlight, including applying the external preparation of any one of <1>, <3> to <7> and <17> to <20> to skin.

<29>

An active oxygen production preventing method in skin, including applying the external preparation of any one of <1>, <3> to <7> and <17> to <20> to skin.

<30>

Use of the external preparation of any one of <1>, <3> to <7> and <17> to <20> as an IR protective external skin preparation.

<31>

Use of the external preparation of any one of <1>, <3> to <7> and <17> to <20> as a heat insulating external skin preparation.

<32>

Use of the external preparation of any one of <1>, <3> to <7> and <17> to <20> as a photoaging preventing external skin preparation.

<33>

Use of the external preparation of any one of <1>, <3> to <7> and <17> to <20> as a skin temperature increase preventing external preparation.

<34>

Use of the external preparation of any one of <1>, <3> to <7> and <17> to <20> as a fatigue preventing external skin preparation.

<35>

Use of the external preparation of any one of <1>, <3> to <7> and <17> to <20> as an active oxygen production preventing external skin preparation.

<36>

An IR protecting method for skin, including applying the external skin preparation of any one of <2> to <16> and <21> to <23> to skin.

<37>

Use of the external preparation of any one of <2> to <16> and <21> to <23> as an IR protective external skin preparation.

EXAMPLES

Hereinunder the present invention is described with reference to Examples, but the present invention is not limited to the range of Examples. In Examples, measurement and evaluation were carried out according to the following methods.

<External Preparations (I)>

(Shape Measurement of Component (A), and Inorganic Particles Except Component (A))

The thickness, the major diameter, the aspect ratio and the average particle size of the component (A) and the inorganic particles except the component (A) (expressed as "component (A)'" in Table 1) were measured by observation with a scanning electron microscope ("VE-9800" from Keyence Corporation) under the condition of an acceleration voltage of 10 keV and an observation power of 10,000 magnifications.

The thickness of the component (A) and the tabular component (A)' was determined by measuring the thickness of 50 particles in an observation image and calculating the average value thereof per number. The aspect ratio was determined by measuring the thickness and the major diameter of 50 particles, then calculating the aspect ratio (major diameter/thickness) of each particle, and averaging the data to give an average value of aspect ratio.

The average particle size of the component (A)' of spherical particles was determined by measuring the particle size of 50 particles of the component followed by averaging the found data.

(IR Protection Factor)

80 mg of the external preparation of each Example was applied onto a glass substrate (5×8 cm) and dried for 15 minutes to give a test sample. For a control sample, glass substrate not coated with an external preparation was prepared. Using a spectrophotometer ("UV-3600" from Shimadzu Corporation) in an integrating sphere mode, the transmissivity at a wavelength of 1500 nm of the test sample and the control sample was measured. A value calculated by dividing the transmissivity of the test sample by the transmissivity of the control sample is referred to as a transmissivity X (%), and 100−X (%) is referred to as an IR protection factor. A larger value means a higher IR protective effect.

(Actual Sense of Heat Insulation on Skin)

In an environment at 28° C. and 40% RH, the external preparation of each Example was applied to the outer side of the forearm in an amount of 2 mg/cm², and dried for 15 minutes. Subsequently, the applied area of the forearm was irradiated with an artificial sunlight source ("SOLAX XC-500EF" from SERIC Ltd.) spaced by 50 cm from the arm for 4 minutes, and the heat immediately after irradiation was evaluated on a five-point scale. Point 1 was given to a scorching feel beyond sufferance, and point 5 was given to a feel with no scorching heat. Five expert panelists tested every sample, and the given points were averaged to be an evaluation result.

<Evaluation Standards>
1: Scorching feel beyond sufferance.
2: Scorching feel.
3: Somewhat scorching feel.
4: Little scorching feel.
5: No scorching feel.

(Spreadability on Skin)

About 0.1 g of the external preparation of each Example was applied to the inner side of the forearm in an area of about 2 cm×5 cm, and evaluated on a five-point scale in point of spreadability on the skin. Point 1 was given to difficult spreadability, and point 5 was given to extremely easy spreadability. Five expert panelists tested every sample, and the given points were averaged to be an evaluation result.

<Evaluation Standards>
1: Difficult spreadability.
2: Somewhat difficult spreadability.
3: Neutral.
4: Somewhat easy spreadability.
5: Extremely easy spreadability.

(Smoothness in Applying to Skin)

About 0.1 g of the external preparation of each Example was applied to the inner side of the forearm in an area of about 2 cm×5 cm, and evaluated on a five-point scale in point of smoothness in applying to the skin. Point 1 was given to unsmooth cases, and point 5 was given to extremely smooth cases. Five expert panelists tested every sample, and the given points were averaged to be an evaluation result.

<Evaluation Standards>
1: Not smooth.
2: Not so much smooth.
3: Neutral.
4: Somewhat smooth.
5: Extremely smooth.

(Comprehensive Evaluation)

In the evaluation results in Table 1, samples having an IR protection factor of 25% or more, an actual sense of heat insulation on skin of 2.5 or more, a spreadability on skin of 3 or more, and smoothness in applying to skin of 3 or more were accepted as good (Evaluation A), while samples not meeting at least any one evaluation item were evaluated as bad (Evaluation C), and the evaluation results are shown in Table 1.

(Anti-Fatigue Effect)

About 1 g of the external preparation of Examples 1-3 and Comparative Example I-1 was applied to the entire face and the forearm, and while the applied parts were irradiated with IR rays from an IR lamp ("Reflamp 250W" from SFC Corporation), the panelists exercised for 5 minutes with an exercise bike ("Program Bike 6215" from ALINCO Incorporated) under a load of 50 W. For the IR irradiation, the distance between the applied parts and the IR lamp was so controlled that the skin temperature could be 42 degrees. The skin temperature was measured with an IR thermograph (T420 from FLIR Corporation).

Immediately after the exercise, every panelist made a self-assessment in point of a feeling of fatigue according to a visual analogue scale (VAS) method. Score 0 was given to no feel of fatigue, and score 100 was given to a completely exhausted fatigue. The given scores were analyzed on a 5-point score according to the following standards to evaluate the anti-fatigue effect. The results are shown in Table 2.

<Evaluation Standards>
1: VAS score 20 or more.
2: VAS score 15 or more and less than 20.
3: VAS score 10 or more and less than 15.
4: VAS score 5 or more and less than 10.
5: VAS score 0 or more and less than 5.

Production Example I-1 (Production of Tabular Titanium Oxide 6)

A toluene solution of 30% by mass tetra-n-butyl orthotitanate (hereinafter referred to as a first liquid) was introduced into a double tube reactor (inner tube opening size 170 µm, outer tube opening size 400 µm) through the inner tube opening at a flow rate of 0.29 ml/min, and a 1-butyl-3-methylimidazolium bis(trifluoromethylsulfonyl)amide solution (hereinafter referred to as a second liquid) with 1% by mass water dissolved therein through the outer tube opening at a flow rate of 20.8 ml/min, and the two liquids were brought into contact with each other for sol-gel reaction to give a gel of tabular titanium oxide. The temperature (reaction temperature) of the first and second liquids was 25° C., and the contact time (reaction time) at the contact area for the first and second liquids was 3 seconds. The resultant slurry was filtered through a metal mesh, and the tabular titanium oxide gel having remained on the metal mesh was washed with ethanol, then dried and fired to give a solid tabular titanium oxide 6. Measured according to the above-mentioned method, the thickness of the tabular titanium oxide 6 was 264 nm and the aspect ratio thereof was 57.

Production Example I-2 (Production of Tabular Titanium Oxide 7)

A tabular titanium oxide 7 was produced in the same manner as in Production Example I-1 except that in Production Example I-1, the flow rate of the first liquid was 0.48 ml/min, and the flow rate of the second liquid was 34.7 ml/min. Measured according to the above-mentioned method, the thickness of the tabular titanium oxide 7 was 300 nm and the aspect ratio thereof was 50.

Production Example I-3 (Production of Comparative Tabular Titanium Oxide 1)

A comparative tabular titanium oxide 1 was produced in the same manner as in Production Example I-1 except that in Production Example I-1, the flow rate of the first liquid was 0.14 ml/min, and the flow rate of the second liquid was 10.4 ml/min. Measured according to the above-mentioned method, the thickness of the comparative tabular titanium oxide 1 was 388 nm and the aspect ratio thereof was 39.

Examples I-1 to 1-10, Comparative Examples I-1 to 1-5 (Production and Evaluation of External Preparations)

All the components shown in Table 1 were blended and mixed uniformly using a disperser to give an external preparation having a composition shown in Table 1. The resultant external preparation was evaluated according to the above-mentioned methods. The results of IR protection factor, actual sense of heat insulation on skin, spreadability on skin, and smoothness in applying to skin are shown in Table 1, and the results of anti-fatigue effect are shown in Table 2. The blending amount shown in Table 1 is the amount (% by mass) of the active ingredient of each component.

TABLE 1

| | | | Example | | | | | | | |
|---|---|---|---|---|---|---|---|---|---|---|
| | | | I-1 | I-2 | I-3 | I-4 | I-5 | I-6 | I-7 | I-8 |
| Formulation of External Preparation (mass %) | (A) | Tabular Titanium Oxide 1 (thickness 66 nm/aspect ratio 227) *1 | 10 | — | — | — | — | — | — | — |
| | | Tabular Titanium Oxide 2 (thickness 100 nm/aspect ratio 150) *2 | — | 10 | — | — | — | — | — | — |
| | | Tabular Titanium Oxide 3 (thickness 112 nm/aspect ratio 134) *3 | — | — | 10 | — | — | — | — | — |
| | | Tabular Titanium Oxide 4 (thickness 134 nm/aspect ratio 112) *4 | — | — | — | 10 | — | — | — | 5 |
| | | Tabular Titanium Oxide 5 (thickness 191 nm/aspect ratio 79) *5 | — | — | — | — | 10 | — | — | — |
| | | Tabular Titanium Oxide 6 (thickness 264 nm/aspect ratio 57) *6 | — | — | — | — | — | 10 | — | — |
| | | Tabular Titanium Oxide 7 (thickness 300 nm/aspect ratio 50) *7 | — | — | — | — | — | — | 10 | — |
| | (A)' | Comparative Tabular Titanium Oxide 1 (thickness 388 nm/aspect ratio 39) *8 | — | — | — | — | — | — | — | — |
| | | Titanium Oxide-Coated Pearl Pigment (tabular, thickness 110 nm/aspect ratio 13) *9 | — | — | — | — | — | — | — | — |
| | | Spherical Titanium Oxide 1 (average particle size 15 nm/aspect ratio 1.0) *10 | — | — | — | — | — | — | — | — |
| | | Spherical Titanium Oxide 2 (average particle size 100 nm/aspect ratio 1.0) *11 | — | — | — | — | — | — | — | — |
| | | Spherical Titanium Oxide 3 (average particle size 200 nm/aspect ratio 1.0) *12 | — | — | — | — | — | — | — | — |
| | | Ethanol | 90 | 90 | 90 | 90 | 90 | 90 | 90 | 95 |
| Evaluation Results | | IR Protection Factor (%) | 42.6 | 48.2 | 56.1 | 55.8 | 55.8 | 46.7 | 30.6 | 27.7 |
| | | Actual Sense of Heat Insulation on Skin | 4.6 | 4.6 | 5 | 5 | 5 | 4.6 | 2.6 | 2.6 |
| | | Spreadability on Skin | 3 | 4 | 4.6 | 5 | 5 | 5 | 4 | 4 |
| | | Smoothness in Applying to Skin | 4 | 4.8 | 4.8 | 5 | 5 | 4.6 | 4 | 4 |
| | | Comprehensive Evaluation | A | A | A | A | A | A | A | A |

| | | | Example | | Comparative Example | | | | |
|---|---|---|---|---|---|---|---|---|---|
| | | | I-9 | I-10 | I-1 | I-2 | I-3 | I-4 | I-5 |
| Formulation of External Preparation (mass %) | (A) | Tabular Titanium Oxide 1 (thickness 66 nm/aspect ratio 227) *1 | — | — | — | — | — | — | — |

TABLE 1-continued

|  |  |  |  |  |  |  |  |  |
|---|---|---|---|---|---|---|---|---|
|  |  | Tabular Titanium Oxide 2 (thickness 100 nm/aspect ratio 150) *2 | — | — | — | — | — | — | — |
|  |  | Tabular Titanium Oxide 3 (thickness 112 nm/aspect ratio 134) *3 | — | — | — | — | — | — | — |
|  |  | Tabular Titanium Oxide 4 (thickness 134 nm/aspect ratio 112) *4 | 7 | 30 | — | — | — | — | — |
|  |  | Tabular Titanium Oxide 5 (thickness 191 nm/aspect ratio 79) *5 | — | — | — | — | — | — | — |
|  |  | Tabular Titanium Oxide 6 (thickness 264 nm/aspect ratio 57) *6 | — | — | — | — | — | — | — |
|  |  | Tabular Titanium Oxide 7 (thickness 300 nm/aspect ratio 50) *7 | — | — | — | — | — | — | — |
|  | (A)' | Comparative Tabular Titanium Oxide 1 (thickness 388 nm/aspect ratio 39) *8 | — | — | 10 | — | — | — | — |
|  |  | Titanium Oxide-Coated Pearl Pigment (tabular, thickness 110 nm/aspect ratio 13) *9 | — | — | — | 10 | — | — | — |
|  |  | Spherical Titanium Oxide 1 (average particle size 15 nm/aspect ratio 1.0) *10 | — | — | — | — | 10 | — | — |
|  |  | Spherical Titanium Oxide 2 (average particle size 100 nm/aspect ratio 1.0) *11 | — | — | — | — | — | 10 | — |
|  |  | Spherical Titanium Oxide 3 (average particle size 200 nm/aspect ratio 1.0) *12 | — | — | — | — | — | — | 10 |
|  |  | Ethanol | 93 | 70 | 90 | 90 | 90 | 90 | 90 |
| Evaluation Results |  | IR Protection Factor (%) | 43.6 | 70.6 | 25.9 | 10.3 | 19.8 | 20.0 | 36.4 |
|  |  | Actual Sense of Heat Insulation on Skin | 4.6 | 5 | 2 | 1.4 | 2 | 2 | 2.4 |
|  |  | Spreadability on Skin | 5 | 5 | 3 | 4 | 1.2 | 2.4 | 2.4 |
|  |  | Smoothness in Applying to Skin | 5 | 5 | 3 | 4 | 1.2 | 1.8 | 2.4 |
|  |  | Comprehensive Evaluation | A | A | C | C | C | C | C |

The blending components in Table 1 are as follows.
*1: "Featheleve PT-9001K" by CQV Co., Ltd.
*2: "Featheleve PT-7001K" by CQV Co., Ltd.
*3: "Featheleve PT-7401K" by CQV Co., Ltd.
*4: "Teatheleve PT-7801K" by CQV Co., Ltd.
*5: "Teatheleve PT-7901K" by CQV Co., Ltd.
*6: Tabular titanium oxide 6 produced in Production Example I-1.
*7: Tabular titanium oxide 7 produced in Production Example I-2.
*8: Comparative tabular titanium oxide 1 produced in Production Example I-3.
*9: Flamenco Satin Blue" by BASF SE (thickness of titanium oxide coating layer: 10 nm).
*10: "MT-100TV" by TAYCA Corporation.
*11: "SOLAVEIL XTP-1" by Croda Japan KK.
*12: "CR-50" by Ishihara Sangyo Kaisha, Ltd.

TABLE 2

| External Preparation | Evaluation Result of Anti-fatigue Effect |
|---|---|
| Example I-3 | 5 |
| Comparative Example I-1 | 3 |

<External Skin Preparation (II)>
(Measurement of Thickness, Major Diameter and Aspect Ratio)

The thickness, the major diameter and the aspect ratio of the component (A) and the inorganic particles except the component (A) (expressed as "component (A)'" in Table 3) were measured by observation with a scanning electron microscope ("VE-9800" from Keyence Corporation) under the condition of an acceleration voltage of 10 keV and an observation power of 10,000 magnifications.

The thickness of the component (A) and the tabular component (A)' was determined by measuring the thickness of 50 particles in an observation image and calculating the average value thereof per number. The aspect ratio was determined by measuring the thickness and the major diameter of 50 particles, then calculating the aspect ratio (major diameter/thickness) of each particle, and averaging the data to give an average value of aspect ratio.

(IR Protection Factor)

28.5 mg of the external skin preparation of each Example was applied onto a polymethyl methacrylate resin (PMMA) substrate ("HD6" from Helioscreen Corporation) of 5 cm×5 cm, and dried for 15 minutes to give a test sample. Similarly, glycerin was applied to a PMMA substrate and dried for 15 minutes to give a control sample. Using a spectrophotometer ("UV-3600" from Shimadzu Corporation) in an integrating sphere mode, the transmissivity at a wavelength of 1500 nm of the test sample and the control sample was measured. A value calculated by dividing the transmissivity of the test sample by the transmissivity of the control sample is referred to as a transmissivity X (%), and 100–X (%) is referred to as an IR protection factor. A larger value means a higher IR protective effect.

(Sense of Natural Appearance when Applied to Skin)

About 0.1 g of the external skin preparation of each Example was applied to the inner side of the forearm in an area of 2 cm×5 cm, and immediately the skin was observed. When the skin was extremely white and gave an unnatural feel, point 1 was given, and when the skin was naturally white with no unnatural feel, point 5 was given, and the tested sample was evaluated on a five-point scale. Five expert panelists tested every sample, and the given points were averaged to be an evaluation result.

<Evaluation Standards>
1: Extremely white, and gave extremely unnatural feel.
2: Somewhat white, and gave an unnatural feel.
3: Neutral.
4: Naturally white, but gave a little unnatural feel.
5: Naturally white, and did not gave an unnatural feel.

(Good Adhesion of Makeup after Applied to Skin)

About 0.1 g of the external skin preparation of each Example was applied to the inner side of the forearm in an area of 2 cm×5 cm, and a powder foundation was applied thereon and evaluated as to "adhesiveness" was given or not. When the applied foundation was non-uniform and was extremely unsmooth, point 1 was given, and when the applied foundation was uniform and was extremely smooth, point 5 was given, and the tested sample was evaluated on a five-point scale. Five expert panelists tested every sample, and the given points were averaged to be an evaluation result.

<Evaluation Standards>
1: Foundation was non-uniform and had bad adhesiveness.
2: Foundation was somewhat non-uniform and had somewhat bad adhesiveness.
3: Neutral.
4: Foundation was somewhat uniform and had somewhat good adhesiveness.
5: Foundation was uniform and had extremely good adhesiveness.

(Comprehensive Evaluation)

In the evaluation results in Table 3, samples having an IR protection factor of 10% or more, a sense of natural appearance when applied to skin of 3.5 or more, and a good adhesion of makeup after applied to skin of 3.5 or more were accepted as good (Evaluation A), while samples not meeting at least any one evaluation item were evaluated as bad (Evaluation C), and the evaluation results are shown in Table 3.

Production Example II-1 (Production of Tabular Titanium Oxide 2)

A toluene solution of 30% by mass tetra-n-butyl orthotitanate (hereinafter referred to as a first liquid) was introduced into a double tube reactor (inner tube opening size 170 μm, outer tube opening size 400 μm) through the inner tube opening at a flow rate of 0.29 ml/min, and a 1-butyl-3-methylimidazolium bis(trifluoromethylsulfonyl)amide solution (hereinafter referred to as a second liquid) with 1% by mass water dissolved therein through the outer tube opening at a flow rate of 20.8 ml/min, and the two liquids were brought into contact with each other for sol-gel reaction to give a gel of tabular titanium oxide. The temperature (reaction temperature) of the first and second liquids was 25° C., and the contact time (reaction time) at the contact area for the first and second liquids was 3 seconds. The resultant slurry was filtered through a metal mesh, and the tabular titanium oxide gel having remained on the metal mesh was washed with ethanol, then dried and fired to give a solid tabular titanium oxide 2. Measured according to the above-mentioned method, the thickness of the tabular titanium oxide 2 was 264 nm and the aspect ratio thereof was 57.

Production Example II-2 (Production of Comparative Tabular Titanium Oxide 1)

A comparative tabular titanium oxide 1 was produced in the same manner as in Production Example II-1 except that in Production Example II-1, the flow rate of the first liquid was 0.14 ml/min, and the flow rate of the second liquid was 10.4 ml/min. Measured according to the above-mentioned method, the thickness of the comparative tabular titanium oxide 1 was 388 nm and the aspect ratio thereof was 39.

Examples II-1 to II-11, Comparative Examples II-1 to II-5 (Production and Evaluation of External Skin Preparations)

Among the components shown in Table 3, all except water and ethanol were blended and mixed uniformly using a disperser. Next, water and ethanol were added to the resultant mixture and uniformly mixed using a homogenizer to give a water-in-oil type external skin preparation having a composition shown in Table 3. The resultant external skin preparation was evaluated according to the above-mentioned methods. The results are shown in Table 3.

The blending amount shown in Table 3 is the amount (% by mass) of the active ingredient of each component.

TABLE 3

|  |  |  |  | Example |  |  |  |  |  |  |  |
|---|---|---|---|---|---|---|---|---|---|---|---|
|  |  |  |  | II-1 | II-2 | II-3 | II-4 | II-5 | II-6 | II-7 | II-8 |
| Formulation of External Preparation (mass %) | (A) | Tabular Titanium Oxide 1 (thickness 134 nm/aspect ratio 112) | *1 | 10 | — | — | 10 | 10 | 5 | 7 | 20 |
|  |  | Tabular Titanium Oxide 2 (thickness 264 nm/aspect ratio 57) | *2 | — | 10 | — | — | — | — | — | — |
|  |  | Tabular Titanium Oxide 3 (thickness 66 nm/aspect ratio 227) | *3 | — | — | 10 | — | — | — | — | — |
|  | (A)' | Comparative Tabular Titanium Oxide 1 (thickness 388 nm/aspect ratio 39) | *4 | — | — | — | — | — | — | — | — |
|  |  | Titanium Oxide-Coated Pearl Pigment (tabular, thickness 110 nm/aspect ratio 13) | *5 | — | — | — | — | — | — | — | — |
|  | (B) | Methylpolysiloxane | *6 | 30 | 30 | 30 | 10 | 40 | 30 | 30 | 30 |
|  |  | Alkyl (C12-15) Benzoate | *7 | — | — | — | — | — | — | — | — |
|  |  | Isopropyl Palmitate | *8 | — | — | — | — | — | — | — | — |
|  |  | Light Liquid Paraffin | *9 | — | — | — | — | — | — | — | — |
|  | (B)' | Decamethylcyclopentasiloxane | *10 | 27.5 | 27.5 | 27.5 | 47.5 | 17.5 | 27.5 | 27.5 | 27.5 |
|  | (C) | Polyoxyethyl-methyl-polysiloxane copolymer | *11 | 0.8 | 0.8 | 0.8 | 0.8 | 0.8 | 0.8 | 0.8 | 0.8 |
|  | Others | Ethanal |  | 11.5 | 11.5 | 11.5 | 11.5 | 11.5 | 11.5 | 11.5 | 11.5 |
|  |  | Water |  | balance | balance | balance | balance | balance | balance | balance | balance |
| Ratio by mass A/B |  |  |  | 0.33 | 0.33 | 0.33 | 1.00 | 0.25 | 0.17 | 0.23 | 0.67 |
| Evaluation Results | IR Protection factor (%) |  |  | 18.2 | 18.0 | 11.5 | 18.0 | 17.0 | 10.6 | 16.5 | 34.8 |
|  | Sense of natural appearance |  |  | 5 | 5 | 4 | 4 | 5 | 5 | 5 | 4 |
|  | Adhesiveness of makeup after applied to skin |  |  | 5 | 5 | 5 | 5 | 4 | 4 | 5 | 4 |
|  | Comprehensive Evaluation |  |  | A | A | A | A | A | A | A | A |

|  |  |  |  | Example |  |  | Comparative Example |  |  |  |  |
|---|---|---|---|---|---|---|---|---|---|---|---|
|  |  |  |  | II-9 | II-10 | II-11 | II-1 | II-2 | II-3 | II-4 | II-5 |
| Formulation of External Preparation (mass %) | (A) | Tabular Titanium Oxide 1 (thickness 134 nm/aspect ratio 112) | *1 | 30 | 10 | 10 | — | — | 10 | 0.5 | 10 |
|  |  | Tabular Titanium Oxide 2 (thickness 264 nm/aspect ratio 57) | *2 | — | — | — | — | — | — | — | — |
|  |  | Tabular Titanium Oxide 3 (thickness 66 nm/aspect ratio 227) | *3 | — | — | — | — | — | — | — | — |
|  | (A)' | Comparative Tabular Titanium Oxide 1 (thickness 388 nm/aspect ratio 39) | *4 | — | — | — | 10 | — | — | — | — |
|  |  | Titanium Oxide-Coated Pearl Pigment (tabular, thickness 110 nm/aspect ratio 13) | *5 | — | — | — | — | 10 | — | — | — |
|  | (B) | Methylpolysiloxane | *6 | 30 | 10 | — | 30 | 30 | — | 30 | 1 |
|  |  | Alkyl (C12-15) Benzoate | *7 | — | 10 | 20 | — | — | — | — | — |
|  |  | Isopropyl Palmitate | *8 | — | 5 | 5 | — | — | — | — | — |
|  |  | Light Liquid Paraffin | *9 | — | 5 | 5 | — | — | — | — | — |
|  | (B)' | Decamethylcyclopentasiloxane | *10 | 27.5 | 27.5 | 27.5 | 27.5 | 27.5 | 57.5 | 57.5 | 57.5 |
|  | (C) | Polyoxyethyl-methyl-polysiloxane copolymer | *11 | 0.8 | 0.8 | 0.8 | 0.8 | 0.8 | 0.8 | 0.8 | 0.8 |
|  | Others | Ethanal |  | 11.5 | 11.5 | 11.5 | 11.5 | 11.5 | 11.5 | 11.5 | 11.5 |
|  |  | Water |  | balance | balance | balance | balance | balance | balance | balance | balance |

TABLE 3-continued

|  |  |  |  |  |  |  |  |  |  |
|---|---|---|---|---|---|---|---|---|---|
| Ratio by mass A/B |  | 1.00 | 0.33 | 0.33 | — | — | — | 0.02 | 10.00 |
| Evaluation Results | IR Protection factor (%) | 40.5 | 17.1 | 16.0 | 6.5 | 8.7 | 16.8 | 2.3 | 16.1 |
|  | Sense of natural appearance | 3.6 | 5 | 5 | 2.4 | 3 | 3 | 3 | 3 |
|  | Adhesiveness of makeup after applied to skin | 3.6 | 5 | 5 | 3 | 5 | 3 | 2 | 3 |
|  | Comprehensive Evaluation | A | A | A | C | C | C | C | C |

The blending components in Table 3 are as follows.
*1: "Featheleve PT-7801K" by CQV Co., Ltd., coated with 7.5% by mass of (alkyl acrylate/dimethicone) copolymer.
*2: Tabular titanium oxide 2 produced in Production Example II-1, coated with 7.5% by mass of (alkyl acrylate/dimethicone) copolymer.
*3: "Featheleve PT-9001K" by CQV Co., Ltd., coated with 7.5% by mass of (alkyl acrylate/dimethicone) copolymer.
*4: Comparative tabular titanium oxide 1 produced in Production Example II-2, coated with 7.5% by mass of (alkyl acrylate/dimethicone) copolymer.
*5: "Flamenco Satin Blue" by BASF SE (thickness of titanium oxide coating layer: 10 nm), coated with 7.5% by mass of (alkyl acrylate/dimethicone) copolymer.
*6: "Silicone KF-96A-10cs" by Shin-Etsu Chemical Co., Ltd.
*7: "Finsolv TN" by Innospec Active Chemicals LLC.
*8: "Exeparl IPP" by Kao Corporation.
*9: "Parleam 4" by NOF Corporation, light liquid isoparaffin (hydrogenated polyisobutene).
*10: "TSF405" by Momentive Performance Materials Corporation.
*11: "SH3775M" by DuPont Toray Specialty Materials K.K., polyoxyethylene-methylpolysiloxane copolymer (PEG-12 dimethicone).

As in Table 3, the external skin preparations of Examples II-1 to II-11 have a good IR protective effect, a good sense of natural appearance when applied to skin, and a good adhesion of makeup after applied to skin. For example, comparing Examples II-1 to II-3 and Comparative Example II-1, it is known that, when a tabular titanium oxide having a predetermined thickness as defined in the present invention is used, there can be provided external skin preparations having a better IR protective effect, and a better sense of natural appearance when applied to skin, and a better adhesion of makeup after applied to skin. In particular, when the component (A) having a thickness falling within a range of 80 nm or more and 280 nm or less is used, the IR protective effect improves more.

As opposed to these, the external skin preparation of Comparative Example II-1 using a tabular titanium oxide whose thickness is more than 360 nm in place of the component (A) has a poor IR protective effect, and the sense of natural appearance when applied to skin and the good adhesion of makeup after applied to skin are also poor. Comparative Example II-2 using tabular inorganic particles except metal oxide in place of the component (A) does not achieve an excellent IR protective effect.

When applied to skin and after applied to skin, the sense of natural appearance and the good adhesion of makeup of the external skin preparation of Comparative Example II-3 not containing the component (B) are poor.

Comparative Example II-4 in which the ratio by mass of the component (A) to the component (B) [(A)/(B)] in the external skin preparation is less than 0.05, and Comparative Example II-5 in which the ratio by mass [(A)/(B)] is more than 5 could not better the sense of natural appearance when applied to skin and the good adhesion of makeup after applied to skin, and in Comparative Example II-4, the IR protective effect is low.

Formulation Example II-1 (Production of External Skin Preparation)

Among the components shown below, all except water and ethanol were blended and mixed uniformly using a disperser. Next, water and ethanol were added to the resultant mixture and uniformly mixed using a homogenizer to give a water-in-oil type emulsion composition of the following formulation (external skin preparation).

|  | (% by mass) |
|---|---|
| (A) Tabular titanium oxide 1 ("Featheleve PT-7801K" by CQV Co., Ltd., coated with 2% by mass of octyltriethoxysilane, thickness 134 nm/aspect ratio 112) | 15.0 |
| (B) Methylpolysiloxane ("Silicone KF-96A-10cs" by Shin-Etsu Chemical Co., Ltd.) | 6.0 |
| (B) Liquid isoparaffin ("Parleam Ex" by NOF Corporation) | 15.0 |
| (B)' Decamethylcyclopentasiloxane ("TSF405 by Momentive Performance Materials Corporation) | 10.0 |
| (C) Polyoxyethylene-methylpolysiloxane copolymer ("Silicone SH3775M" by DuPont Toray Specialty Materials K.K.) | 1.0 |
| N-propionylpolyethyleneimine-methylpolysiloxane copolymer ("Polysilicone-9" by Kao Corporation) | 0.2 |
| UV absorbent | 10.0 |
| (2-ethylhexyl paramethoxycinnamate, "Uvinul MC80" by BASF SE) |  |
| (Bis-ethylhexyloxyphenol methoxyphenyl triazine, "Tinosorb S" by BASF SE) | 2.0 |
| Titanium oxide ("JR-1000" by TAYCA Corporation) | 5.0 |
| Ethanol | 10.0 |
| Glycerin | 1.0 |
| Water | balance |
| Total | 100.0 |

(Ratio by mass (A)/(B) = 0.71)

Formulation Example II-2 (Production of External Skin Preparation)

Among the components shown below, water, 1,3-butylene glycol and ethanol were put into a blending tank and stirred to give an aqueous phase. On the other hand, at a temperature around 80° C., the remaining components were mixed to prepare an oily phase. The oily phase was added to the aqueous phase, then uniformly mixed with a homogenizer, and cooled to give an oil-in-water type emulsion composition of the following formulation (external skin preparation).

| | (% by mass) |
|---|---|
| (A) Tabular titanium oxide 1 ("Featheleve PT-7801K" by CQV Co., Ltd., coated with 2.5% by mass of octyltriethoxysilane, thickness 134 nm/aspect ratio 112) | 8.0 |
| (B) Neopentyl glycol dicaprylate ("Estemol N-01" by The Nisshin OilliO Group. Ltd. | 5.0 |
| (B)' Decamethylcyclopentasiloxane ("TSF405 by Momentive Performance Materials Corporation) | 3.0 |
| (C) Polyoxyethylene sorbitan monostearate (Rheodol TW-S120V" by Kao Corporation) | 0.6 |
| (C) Sorbitan stearate (Rheodol SP-S10V" by Kao Corporation) | 0.6 |
| Emulsifier ((Sodium acrylate/Sodium acryloyldimethyl taurate) copolymer dispersion, "SIMULGEL EG" by Seppic Corporation) | 1.5 |
| UV absorbent (2-Ethylhexyl paramethoxycinnamate, "Uvinul MC80" by BASF SE) | 10.0 |
| (Bis-ethylhexyloxyphenol methoxyphenyl triazine, "Tinosorb S" by BASF SE) | 1.0 |
| UV scattering agent (Aluminum hydroxide/stearic acid-coated titanium oxide fine particles, "MT-100TV" by TAYCA Corporation) | 3.0 |
| Ethanol | 10.0 |
| 1,3-Butylene glycol | 1.0 |
| Water | balance |
| Total | 100.0 |

(Ratio by mass (A)/(B) = 1.6)

Formulation Example II-3 (Production of External Skin Preparation)

Among the components shown below, water, (acrylates/alkyl acrylate (C10-30)) crosspolymer, 1,3-butylene glycol and ethanol were put into a blending tank and stirred to give an aqueous phase. On the other hand, at a temperature around 80° C., the remaining components except potassium hydroxide of the following components were mixed to prepare an oily phase. The oily phase was added to the aqueous phase, stirred, and potassium hydroxide was added, uniformly mixed with a homogenizer, and cooled to give an oil-in-water type emulsion composition of the following formulation (external skin preparation).

| | (% by mass) |
|---|---|
| (A) Tabular titanium oxide 1 ("Featheleve PT-7801K" by CQV Co., Ltd., coated with 2.5% by mass of octyltriethoxysilane, thickness 134 nm/aspect ratio 112) | 10.0 |
| (B) Isopropyl palmitate ("Exeparl IPP" by Kao Corporation") | 3.0 |
| (B) Methylpolysiloxane ("Silicone KF-96A-10cs" by Shin-Etsu Chemical Co., Ltd.) | 1.0 |
| (C) Polyoxyethylene sorbitan monostearate ("Rheodol TW-S120V" by Kao Corporation) | 0.1 |
| Thickener (Acrylates/alkyl (C10-30) acrylate)) crosspolymer, "PUMULEN TR-1" by Lubrizol Corp.) | 0.4 |
| Oil gelling agent (Dextrin palmitate, "Rheopearl KL2" by Chiba Flour Milling Co., Ltd.) | 1.0 |
| UV absorbent (2-Ethylhexyl paramethoxycinnamate, "Uvinul MC80" by BASF SE) | 8.0 |
| (Bis-ethylhexyloxyphenol methoxyphenyl triazine, "Tinosorb S" by BASF SE) | 2.0 |
| UV scattering agent (Aluminum hydroxide/stearic acid-coated titanium oxide fine particles, "MT-100TV" by TAYCA Corporation) | 5.0 |
| Ethanol | 5.0 |
| 1,3-Butylene glycol | 3.0 |

| | (% by mass) |
|---|---|
| Potassium hydroxide | 0.25 |
| Water | balance |
| Total | 100.0 |

(Ratio by mass (A)/(B) = 2.5)

INDUSTRIAL APPLICABILITY

The external preparations (I) of the present invention are excellent in an IR protective effect and can achieve an actual sense of high-level heat insulation, and also have good spreadability on skin and good smoothness after applied to skin. By applying the external preparations of the present invention to skin, there can be achieved an effect of insulating skin from heat, an effect of protecting skin from photoaging, an effect of preventing skin temperature increase, an effect of preventing skin from being fatigued by irradiation with sunlight, and an effect of preventing active oxygen production in skin.

The external skin preparation (II) of the present invention is excellent in an IR protective effect, and when applied to skin, it hardly whitens and can give a natural appearance, and after applied to skin, it secures a good adhesion of makeup and gives a good sense of use, and accordingly, the external skin preparation is useful, for example, as a skin cosmetic material.

The invention claimed is:

1. An external preparation, comprising:
a tabular metal oxide (A) which is tabular titanium oxide having a thickness of 30 nm or more and 360 nm or less; and
a nonvolatile oil (B),
wherein a content of the tabular metal oxide (A) is 1% by mass or more and 35% by mass or less,
wherein a content of the nonvolatile oil (B) is 10% by mass or more,
wherein a ratio by mass of the tabular metal oxide (A) to the nonvolatile oil (B) is 0.05 or more and 5 or less,
wherein the external preparation is a water-in-oil type emulsion composition, and
wherein the external preparation has an IR protection factor of 10% or more, which is 100%–the percentage fraction of transmissivity at 1500 nm wavelength of 28.5 mg of the external preparation applied and dried on a 5 cm×5 cm polymethyl methacrylate resin substrate relative to the transmissivity at 1500 nm wavelength of the polymethyl methacrylate resin substrate with glycerin applied and dried.

2. The external preparation according to claim 1, wherein an aspect ratio of the tabular metal oxide (A) is 50 or more and 300 or less.

3. An external preparation, comprising:
a tabular metal oxide (A) which is tabular titanium oxide having a thickness of 30 nm or more and 360 nm or less and an aspect ratio of 50 or more and 300 or less; and
a nonvolatile oil (B),
wherein a content of the tabular metal oxide (A) is 1% by mass or more and 35% by mass or less,
wherein a content of the nonvolatile oil (B) is 10% by mass or more,
wherein a ratio by mass of the tabular metal oxide (A) to the nonvolatile oil (B) is 0.05 or more and 5 or less,
wherein the external preparation is a water-in-oil type emulsion composition, and
wherein the external preparation has an IR protection factor of 10% or more, which is 100%–the percentage fraction of transmissivity at 1500 nm wavelength of 28.5 mg of the external preparation applied and dried on a 5 cm×5 cm polymethyl methacrylate resin substrate relative to the transmissivity at 1500 nm wavelength of the polymethyl methacrylate resin substrate with glycerin applied and dried.

4. The external preparation according to claim 1, wherein the tabular metal oxide (A) further comprises tabular zinc oxide.

5. The external preparation according to claim 3, wherein the nonvolatile oil (B) is one or more selected from the group consisting of an ester oil, a silicone oil, a hydrocarbon oil, a higher fatty acid, and a higher alcohol.

6. The external preparation according to claim 3, wherein a content of the nonvolatile oil (B) is from 10% by mass to 30% by mass.

7. A method for protecting skin from IR ray, the method comprising applying the external preparation of claim 1 to skin.

8. A method for insulating skin from heat, the method comprising applying the external preparation of claim 1 to skin.

9. A method for protecting skin from photoaging, the method comprising applying the external preparation of claim 1 to skin.

10. A method for preventing skin temperature increase, the method comprising applying the external preparation of claim 1 to skin.

11. A method for preventing skin from being fatigued owing to irradiation with sunlight, the method comprising applying the external preparation of claim 1 to skin.

12. A method for preventing active oxygen production in skin, the method comprising applying the external preparation of claim 1 to skin.

13. A method for protecting skin from IR ray, the method comprising applying the external preparation of claim 3 to skin.

* * * * *